(12) United States Patent
Tanaka et al.

(10) Patent No.: US 8,147,402 B2
(45) Date of Patent: Apr. 3, 2012

(54) ENDOSCOPE SYSTEM

(75) Inventors: Hideki Tanaka, Tama (JP); Jun Hasegawa, Hino (JP); Toshio Nakamura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 205 days.

(21) Appl. No.: 12/763,514

(22) Filed: Apr. 20, 2010

(65) Prior Publication Data

US 2010/0204545 A1 Aug. 12, 2010

Related U.S. Application Data

(63) Continuation of application No. PCT/JP2008/068789, filed on Oct. 16, 2008.

(30) Foreign Application Priority Data

| Nov. 29, 2007 | (JP) | 2007-309232 |
| Nov. 29, 2007 | (JP) | 2007-309233 |
| Dec. 7, 2007 | (JP) | 2007-317369 |

(51) Int. Cl.
*A61B 1/00* (2006.01)
*A61B 1/04* (2006.01)
(52) U.S. Cl. ......... 600/117; 600/118; 600/146; 600/103
(58) Field of Classification Search .................. 600/117, 600/118, 103, 146; 382/128
See application file for complete search history.

(56) References Cited

U.S. PATENT DOCUMENTS

| 5,658,238 | A * | 8/1997 | Suzuki et al. ................. 600/150 |
| 7,277,833 | B2 * | 10/2007 | Kukuk ............................. 703/2 |
| 8,038,605 | B2 * | 10/2011 | Tsuji et al. .................... 600/152 |
| 2005/0020878 | A1 * | 1/2005 | Ohnishi et al. ............... 600/117 |
| 2005/0085717 | A1 * | 4/2005 | Shahidi ......................... 600/424 |
| 2005/0165276 | A1 | 7/2005 | Belson et al. |
| 2005/0245803 | A1 | 11/2005 | Glenn Jr. et al. |
| 2006/0015011 | A1 * | 1/2006 | Hasegawa et al. ............. 600/117 |

(Continued)

FOREIGN PATENT DOCUMENTS
JP 5-228102 9/1993
(Continued)

OTHER PUBLICATIONS

Extended Supplementary European Search Report dated May 27, 2011.

(Continued)

*Primary Examiner* — John P Leubecker
(74) *Attorney, Agent, or Firm* — Scully, Scott, Murphy & Presser, P.C.

(57) ABSTRACT

An endoscope system of the invention includes: an endoscope including an insertion portion, a distal end portion provided on a distal end side of the insertion portion, and a bending portion which is capable of changing a position and an orientation of the distal end portion; a position detecting section for acquiring position information on a position where the distal end portion is located; a passing target position setting section for setting a passing target position for the distal end portion; a path estimating section for estimating a path through which the distal end portion is to be passed; a bending control target position setting section for setting a bending control target position such that the distal end portion reaches the passing target position along the path; and a bending control information calculating section for calculating an amount of bending and a bending direction of the bending portion.

3 Claims, 16 Drawing Sheets

U.S. PATENT DOCUMENTS

| | | | | |
|---|---|---|---|---|
| 2007/0106116 | A1* | 5/2007 | Sugimoto | 600/117 |
| 2007/0293721 | A1* | 12/2007 | Gilboa | 600/117 |
| 2009/0074268 | A1* | 3/2009 | Tanaka et al. | 382/128 |
| 2009/0259099 | A1* | 10/2009 | Zhou et al. | 600/109 |

FOREIGN PATENT DOCUMENTS

| | | |
|---|---|---|
| JP | 7-155289 | 6/1995 |
| JP | 11-337845 | 12/1999 |
| JP | 2005-520590 | 7/2005 |
| JP | 2006-116289 | 5/2006 |
| JP | 2007-185356 | 7/2007 |
| WO | WO 03/077758 A1 | 9/2003 |

OTHER PUBLICATIONS

International Search Report dated Jan. 20, 2009.

* cited by examiner

DARK PART REGION

DARK PART REGION

ENDOSCOPE SYSTEM

CROSS REFERENCE TO RELATED APPLICATION

This application is a continuation application of PCT/JP2008/068789 filed on Oct. 16, 2008 and claims the benefit of Japanese Applications No. 2007-309232 filed in Japan on Nov. 29, 2007, No. 2007-309233 filed in Japan on Nov. 29, 2007, and No. 2007-317369 filed in Japan on Dec. 7, 2007, the entire contents of each of which are incorporated herein by their reference.

BACKGROUND OF THE INVENTION

1. Field of the Invention

The present invention relates to an endoscope system, and more particularly to an endoscope system capable of performing bending control on an endoscope including a bending portion.

2. Description of the Related Art

Conventionally, endoscopes have been widely used in medical and industrial fields. In the medical field, for example, endoscopes are used for performing observation and various kinds of treatment on living tissues and the like.

Furthermore, when observation and various kinds of treatment are performed on a lower digestive tract by inserting an insertion portion from an anus side of a subject, in order to smoothly insert the insertion portion in a flexed lumen, an endoscope insertion shape detecting apparatus, which is capable of detecting, for example, a position of the insertion portion in a body cavity and a flexing state (bending state) of the insertion portion, is used together with the endoscope.

In recent years, Japanese Patent Application Laid-Open Publication No. 2006-116289 has proposed a bending control apparatus which is capable of selecting and executing bending control corresponding to either an endoscopic image acquired by an endoscope including a bending portion or an insertion shape image of the endoscope acquired by the endoscope insertion shape detecting apparatus.

Furthermore, endoscopes used in the medical field includes, for example, an elongated insertion portion configured to be insertable in a body cavity, a distal end portion provided on a distal end side of the insertion portion and having an image pickup section capable of picking up an image of a subject in the body cavity, and a bending portion which is connected to the distal end portion and which is capable of changing the position and orientation of the distal end portion with respect to the insertion direction of the insertion portion.

For example, Japanese Patent Application Laid-Open Publication No. 7-155289 discloses a technique applicable to the assistance of the bending operation of the above-described bending portion.

The Japanese Patent Application Laid-Open Publication No. 7-155289 proposes an endoscope apparatus which is capable of performing control such that, after extracting a dark part region from an image acquired by an endoscope, the distal end portion of the endoscope is advanced toward the center portion of the dark part region.

SUMMARY OF THE INVENTION

An endoscope system according to the present invention includes: an endoscope including an insertion portion to be inserted in a subject, a distal end portion which is provided on a distal end side of the insertion portion and which includes an image pickup section for outputting an image pickup signal corresponding to an image of a photographic subject in the subject, and a bending portion which is capable of changing a position and an orientation of the distal end portion with respect to an insertion direction of the insertion portion; a position detecting section for acquiring position information including at least information on a position where the distal end portion is located; a passing target position setting section for setting a passing target position for the distal end portion based on the image of the photographic subject; a path estimating section for estimating a path through which the distal end portion is to be passed based on the position information and the passing target position; a bending control target position setting section for properly setting a bending control target position on the path such that the distal end portion reaches the passing target position along the path, based on the passing target position and the path; and a bending control information calculating section for calculating bending control information on an amount of bending and a bending direction of the bending portion based on the bending control target position.

An endoscope system according to the present invention includes: an endoscope including an insertion portion to be inserted in a subject, a distal end portion which is provided on a distal end side of the insertion portion and which includes an image pickup section for outputting an image pickup signal corresponding to an image of a photographic subject in the subject, and a bending portion which is capable of changing a position and an orientation of the distal end portion with respect to an insertion direction of the insertion portion; a position detecting section for acquiring position information including at least information on a position where the distal end portion is located; a dark part region detecting section for detecting a shape of a dark part region included in the image of the photographic subject; a target position setting section for setting a target position for the distal end portion to be passed as a position corresponding to the shape of the dark part region, based on a detection result from the dark part region detecting section; and a bending control information calculating section for calculating bending control information on an amount of bending and a bending direction of the bending portion based on the target position and the position information.

An endoscope system according to the present invention includes: an endoscope including an insertion portion to be inserted in a lumen, a distal end portion which is provided on a distal end side of the insertion portion and which includes an image pickup section for outputting an image pickup signal corresponding to an image of a photographic subject in the lumen, and a bending portion which is capable of changing a position and an orientation of the distal end portion with respect to an insertion direction of the insertion portion; a three-dimensional shape calculating section for calculating three-dimensional shape data of the lumen based on a two-dimensional image of the photographic subject; a cutting surface acquiring section for acquiring a plurality of cutting surfaces of the lumen based on the three-dimensional shape data; and a path calculating section for detecting a path point corresponding to a cross-sectional shape of each of the plurality of cutting surfaces on each of the plurality of cutting surfaces, and calculating a path formed by at least connecting each path point and a distal end surface of the distal end portion; a target position setting section for setting on the path a target position for the distal end portion to be passed; and a bending control information calculating section for calculating bending control information on an amount of bending and a bending direction of the bending portion based on the target position.

DETAILED DESCRIPTION OF THE PREFERRED EMBODIMENT(S)

Hereinafter, embodiments of the present invention will be described with reference to the drawings.

(First Embodiment)

Figure 1:
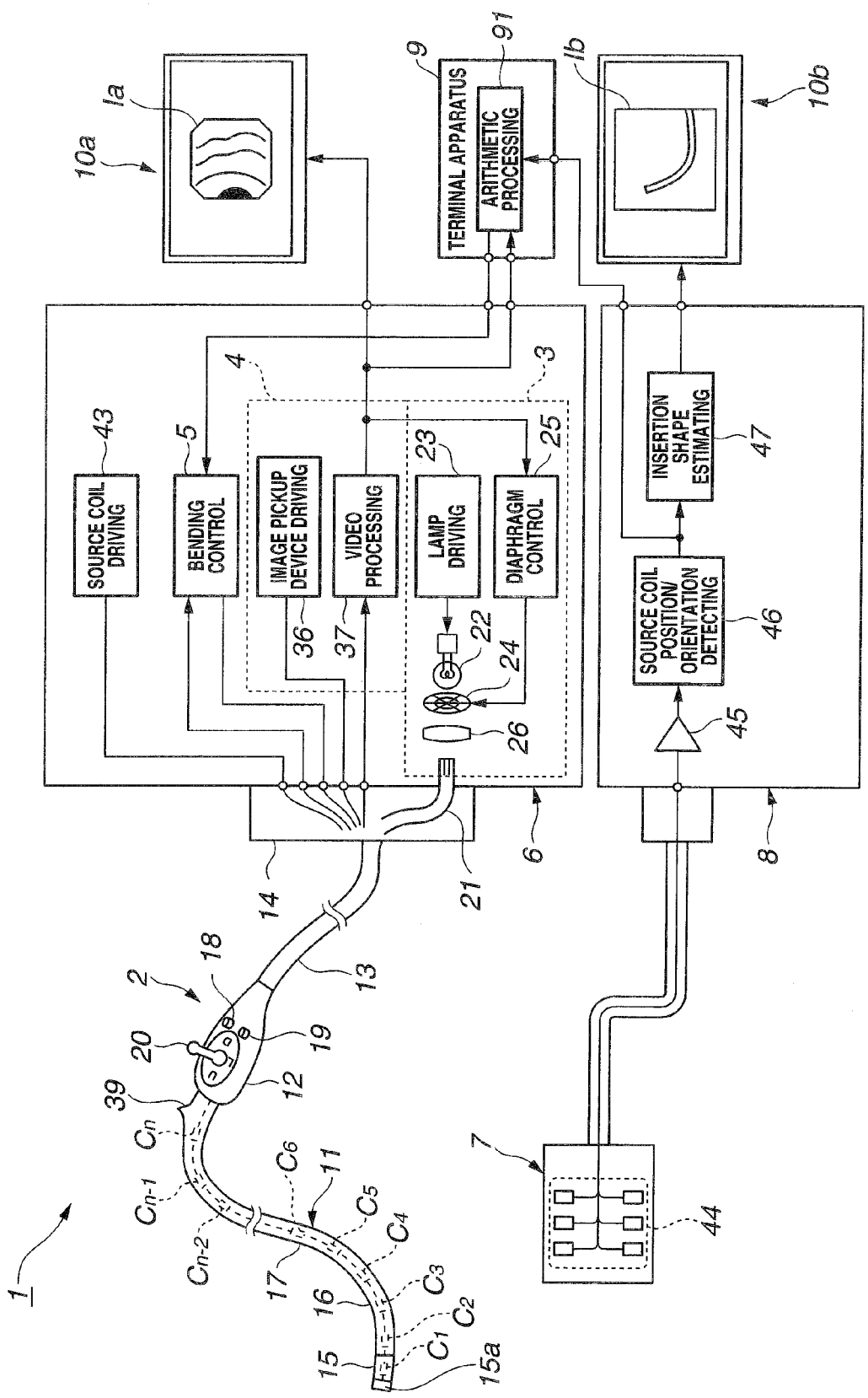
FIG. 1 is a view showing a configurational example of a main part of an endoscope system according to a first embodiment of the present invention.
Figure 2:
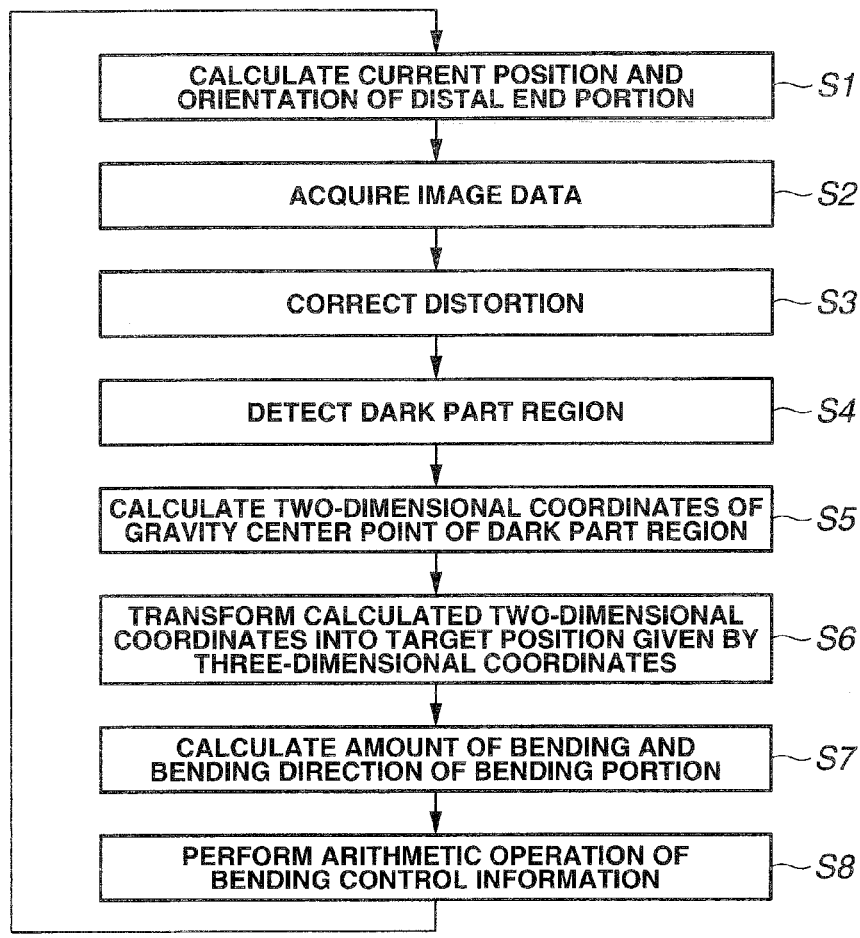
FIG. 2 is a flowchart showing an example of processing performed for setting a passing target position for a distal end portion and a content of bending control with respect to a bending portion.
Figure 3:
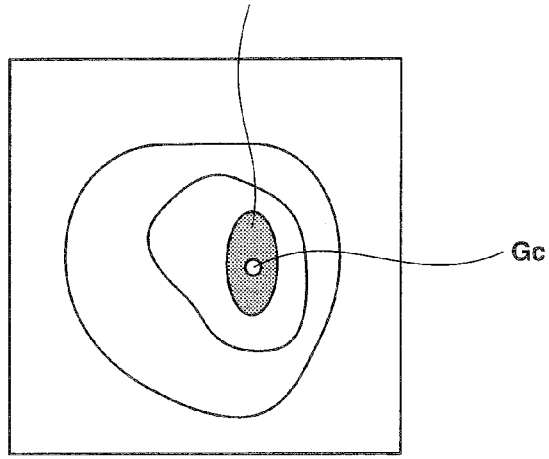
FIG. 3 is a view showing an example of a dark part region existing in image data.
Figure 4:
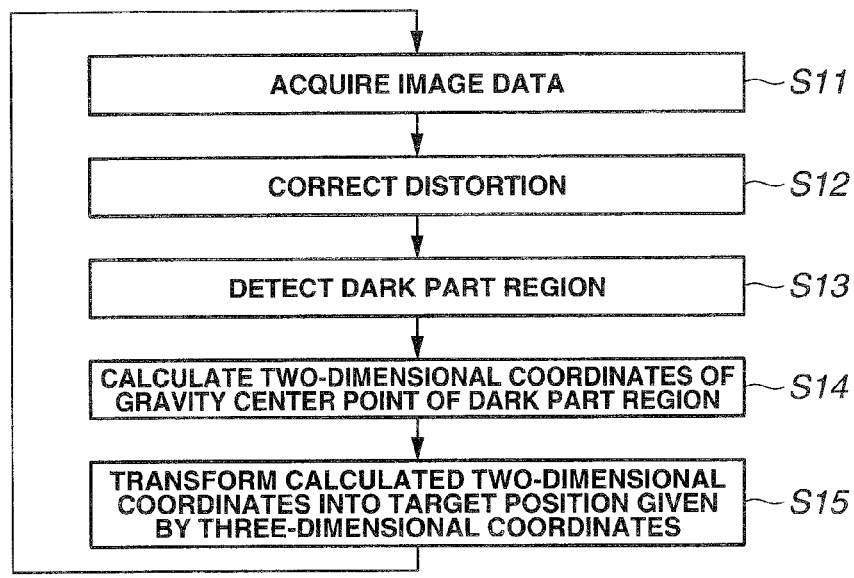
FIG. 4 is a flowchart showing a modified example of the processing performed for setting the passing target position for the distal end portion.
Figure 5:
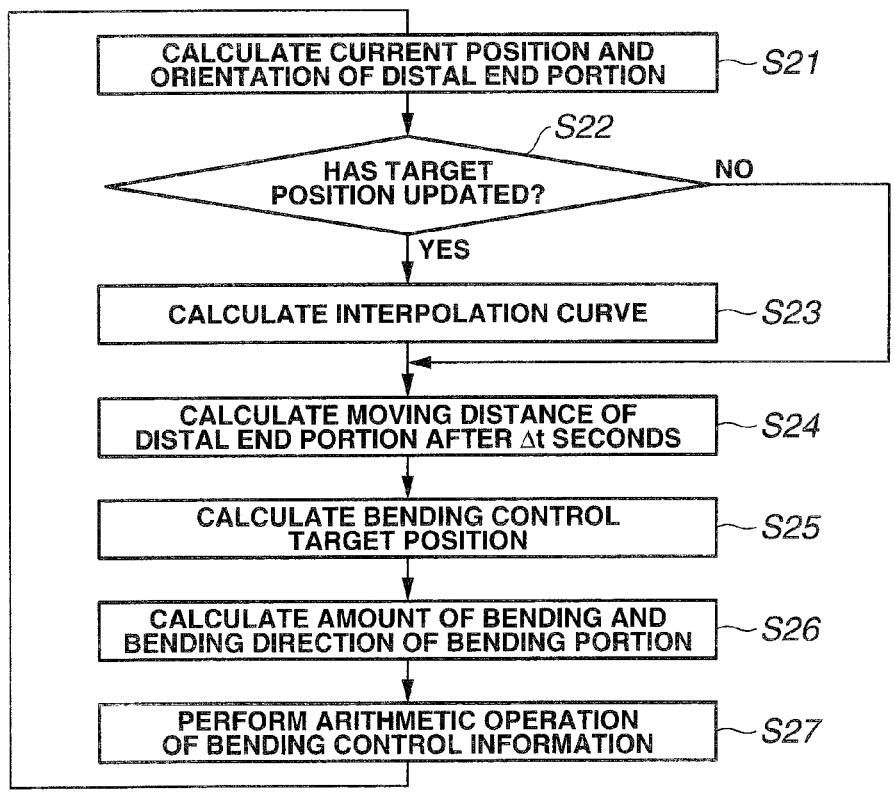
FIG. 5 is a flowchart showing a modified example of the processing performed for setting the content of bending control with respect to the bending portion.
Figure 6:
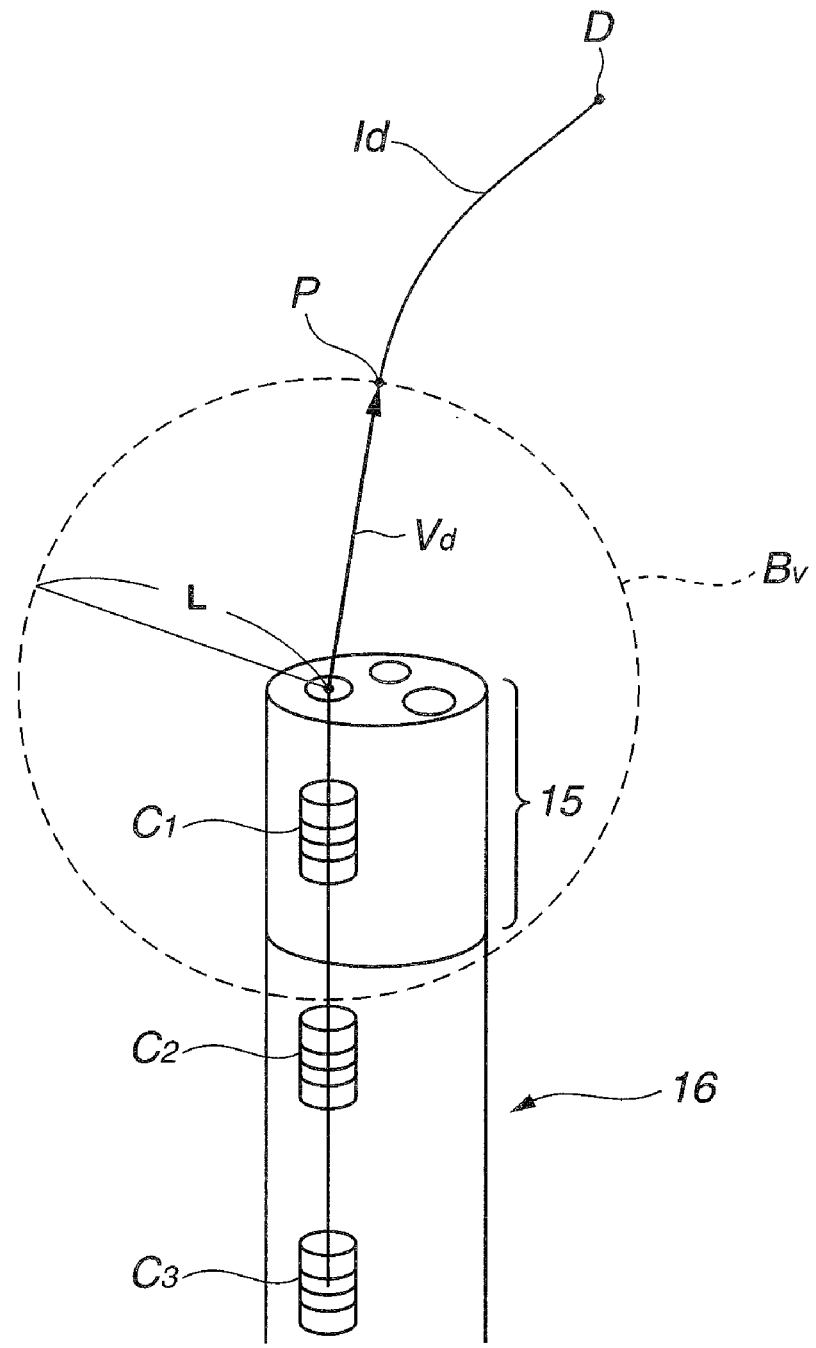
FIG. 6 is a schematic diagram showing a brief overview of the processing shown in the flowcharts in FIG. 4 and FIG. 5.

FIG. 1 is a view showing a configurational example of a main part of an endoscope system according to the first embodiment of the present invention. FIG. 2 is a flowchart showing an example of processing performed for setting a passing target position for a distal end portion and content of bending control with respect to a bending portion. FIG. 3 is a view showing an example of a dark part region existing in image data. FIG. 4 is a flowchart showing a modified example of the processing performed for setting the passing target position for the distal end portion. FIG. 5 is a flowchart showing a modified example of the processing performed for setting the content of bending control with respect to the bending portion. FIG. 6 is a schematic diagram showing a brief overview of the processing shown in the flowcharts in FIG. 4 and FIG. 5.

As shown in FIG. 1, an endoscope system 1 according to the first embodiment of the present invention includes: an endoscope 2 configured to be inserted into a body cavity of a patient as a subject and pick up an image of the subject in a body cavity; a processor 6 to and from which a connector 14 provided to the endoscope 2 is attachable and detachable; a sense coil unit 7 arranged around a bed on which a patient lies; an endoscope insertion shape detecting apparatus 8; a terminal apparatus 9; a monitor 10a; and a monitor 10b.

Furthermore, the processor 6 includes: a light source section 3 that supplies illumination light for illuminating a photographic subject as an image pickup object to the endoscope 2; a signal processing section 4 that generates a video signal by performing signal processing on an image pickup signal outputted from the endoscope 2 and outputs the generated video signal; a bending control section 5 that performs bending control on the endoscope 2; and a source coil driving section 43.

The endoscope 2 includes an elongated insertion portion 11 to be inserted in the body cavity of the subject, an operation portion 12 provided at a rear end of the insertion portion 11, and a universal cord 13 extended from the operation portion 12. The connector 14 that is attachable to and detachable from the processor 6 is provided at a rear end of the universal cord 13.

The insertion portion 11 includes: a rigid distal end portion 15 provided on a distal end side; a bending portion 16 connected to a rear end of the distal end portion 15; and a flexible tube portion 17 having flexibility that is provided between a rear end of the bending portion 16 and a front end of the operation portion 12. Furthermore, n-pieces of source coils $C_1, C_2, \ldots,$ and $C_n$ that generate magnetic fields corresponding to the source coil driving signals applied by the source coil driving section 43 are provided in the insertion portion 11 at substantially equal intervals.

The distal end portion 15 is provided with an image pickup section 15a including an objective optical system that forms an image of a photographic subject and an image pickup device that outputs the image of the photographic subject formed through the objective optical system as an image pickup signal.

The operation portion 12 is provided with a scope switch 18 that gives an instruction for acquiring a freeze image (still image), for example; a bending mode switching switch 19 that gives an instruction for switching the bending mode of the bending portion 16 to either the manual bending mode or the automatic bending mode; a joystick 20 for bending operation that gives instructions on the bending direction and the bending angle of the bending portion 16 when the manual bending mode is selected. In addition, at a portion on a rear end side of the flexible tube portion 17 and near the front end of the operation portion 12 is provided a treatment instrument insertion port 39 leading to a channel for treatment instrument, not shown, through which a treatment instrument or the like is insertable.

A light guide 21 that transmits the illumination light supplied from the light source section 3 to the distal end portion 15 is inserted in the insertion portion 11 and the like of the endoscope 2.

One end surface (incident end surface) of the light guide 21 is arranged protruding from the connector 14. Furthermore, the other end surface (light-emitting end surface) of the light guide 21 is arranged in the vicinity of an illumination optical system, not shown, provided in the distal end portion 15. According to such a configuration, in a state where the connector 14 is connected to the processor 6, the illumination light supplied from the light source section 3 passes through the light guide 21 and the illumination optical system, not shown, and thereafter illuminates the photographic subject as the image pickup object of the image pickup section 15a.

The light source portion 3 includes: a lamp 22 that emits illumination light which is white light, for example; a lamp driving section 23 that supplies a power source required for driving the lamp 22; a diaphragm 24; a diaphragm control section 25 that increases and decreases the diaphragm amount (opening amount) of the diaphragm 24 based on the video signal outputted from the signal processing section 4; a light condensing optical system 26 that condenses the illumination light which passed through the diaphragm 24 and supplies the illumination light to the incident end surface of the light guide 21.

The diaphragm control section 25, for example, calculates the average brightness based on the luminance components of the video signal inputted thereto, and thereafter appropriately changes the light amount of the illumination light passing through the diaphragm 24 by increasing or decreasing the diaphragm amount (opening amount) of the diaphragm 24 based on a difference value which is a value obtained by subtracting a reference value corresponding to the appropriate brightness from the average brightness.

The signal processing section 4 includes an image pickup device driving section 36 that outputs an image pickup device driving signal for driving the image pickup device provided in the image pickup section 15a, and a video processing section 37 that generates a video signal by performing signal processing on the image pickup signal outputted from the image pickup section 15a and outputs the generated video signal. According to this configuration, an endoscopic image Ia1 based on the video signal is displayed on the monitor 10a.

When the bending mode of the bending portion 16 is switched to the manual bending mode based on the instruction given by the bending mode switching switch 19, the bending control section 5 performs control to change the bending direction and the bending angle of the bending portion 16 based on the inclination direction and the inclination amount of the joystick 20 for bending operation. In addition, when the bending mode of the bending portion 16 is switched to the automatic bending mode based on the instruction given by the bending mode switching switch 19, the bending control section 5 performs control to change the bending direction and the bending angle of the bending portion 16 based on the arithmetic operation result of the terminal apparatus 9.

The source coil driving section 43 is connected to the n-pieces of source coils $C_1, C_2, \ldots,$ and $C_n$ provided in the insertion portion 11, and sequentially applies an alternate current source coil driving signal to each of the source coils. As a result, an alternate current magnetic field is generated around each of the source coils provided in the insertion portion 11.

The sense coil unit 7 is provided with a sense coil group 44 that detects the magnetic field generated from each of the n-pieces of source coils $C_1, C_2, \ldots,$ and $C_n$ provided in the insertion portion 11 and outputs the detected magnetic fields as magnetic field detection signals.

The endoscope insertion shape detecting apparatus 8 includes: an amplifier 45 that amplifies the magnetic field detection signals outputted from the sense coil unit 7; a source coil position/orientation detecting section 46 that detects three-dimensional coordinate positions and orientations of the n-pieces of source coils $C_1, C_2, \ldots,$ and $C_n$ based on the magnetic field detection signals outputted from the amplifier 45, and outputs the detected three-dimensional coordinate positions and orientations as insertion shape information; an insertion shape estimating section 47 that estimates the insertion shape of the insertion portion 11 based on the insertion shape information outputted from the source coil position/orientation detecting section 46, and outputs the estimated insertion shape as an insertion shape image signal. According to this configuration, an insertion shape image Ib1 of the insertion portion 11 based on the insertion shape image signal is displayed on the monitor 10b.

The terminal apparatus 9 includes an arithmetic processing section 91 that performs arithmetic operation related to the bending control performed in a case where the bending mode of the bending portion 16 is the automatic mode, based on the video signal outputted from the video processing section 37 and the insertion shape information outputted from the source coil position/orientation detecting section 46, and outputs the arithmetic operation result to the bending control section 5. Note that the specific content of the arithmetic operation performed in the arithmetic processing section 91 will be described later.

Next, description will be made on the working of the endoscope system 1. Note that description on the control in the case where the bending mode switching switch 19 is switched to the manual bending mode will be omitted below, and description will be mainly made on the control in the case where the bending mode switching switch 19 is switched to the automatic bending mode.

First, an operator connects and activates each of the parts of the endoscope system 1, and thereafter inserts the insertion portion 11 of the endoscope 2 into a body cavity of a patient and switches the bending mode switching switch 19 to the automatic bending mode. In response to this, the image pickup section 15a in the endoscope 2 starts picking up an image of a photographic subject, and each of the source coils provided in the insertion portion 11 starts to generate a magnetic field.

The image pickup signal outputted from the image pickup section 15a in association with the image pickup of the photographic subject is outputted to the processor 6, through the universal cord 13 and the connector 14, to be converted into a video signal in the video processing section 37, and thereafter inputted to the arithmetic processing section 91 in the terminal apparatus 9. In addition, the magnetic field detection signals outputted from the sense coil unit 7 in association with the generation of magnetic fields from the source coils provided in the insertion portion 11 are amplified by the amplifier 45, to be converted as the three-dimensional coordinate information of the source coils by the source coil position/orientation detecting section 46, and thereafter inputted to the arithmetic processing section 91 in the terminal apparatus 9.

The arithmetic processing section 91 in the terminal apparatus 9 performs processing based on the inputted video signal and the inputted three-dimensional coordinate information of the source coils, thereby setting a target position which is a passing target for the distal end portion 15 and setting the control content for bending the bending portion 16 such that the distal end portion 15 is directed in the direction of the target position.

Now, description will be made on the processing performed by the arithmetic processing section 91 in order to set the target position and the control content with reference to FIG. 2 and FIG. 3.

The arithmetic processing section 91 calculates the current position and orientation of the distal end portion 15 based on the three-dimensional coordinate information outputted from the source coil position/orientation detecting section 46 (step S1 in FIG. 2).

In addition, the arithmetic processing section 91 acquires image data based on the video signal inputted thereto (step S2 in FIG. 2), and thereafter performs distortion correction on the image data (step S3 in FIG. 2). According to such processing, the arithmetic processing section 91 acquires the image data in which a monochrome portion is eliminated from the original image based on the inputted video signal.

Then, the arithmetic processing section 91 uses the method disclosed in Japanese Patent Application Laid-Open Publication No. 2-203831, for example, to detect the dark part region in the image data acquired in the processing in the step S3 in FIG. 2 (step S4 in FIG. 2). Note that the arithmetic processing section 91 may use other method as the method of detecting the dark part region in the image instead of the method disclosed in Japanese Patent Application Laid-Open Publication No. 2-203831.

The arithmetic processing section 91 calculates the two-dimensional coordinates of a gravity center point of the dark part region based on the dark part region detected by the processing in the step S4 in FIG. 2 (step S5 in FIG. 2). Specifically, the arithmetic processing section 91 calculates the two-dimensional coordinates of a gravity center point Gc of the dark part region in the image data in which the dark part region as shown in FIG. 3, for example, exists. Note that, as the processing for calculating the two-dimensional coordinates of the gravity center point of the dark part region, the arithmetic processing section 91 may perform the processing by regarding a centroid calculated according to sequence of points existing on the edge of the dark part region as the gravity center point, or may calculate the gravity center point using a 0th moment and the primary moment of the dark part region.

After that, the arithmetic processing section 91 transforms the two-dimensional coordinates of the gravity center point Gc which was calculated in the processing in step S5 in FIG. 2 into the target position given by the three-dimensional coordinates by using the Shape From Shading method and the like, for example (step S6 in FIG. 2).

That is, the arithmetic processing section 91 sets a target three-dimensional coordinate position such that the distal end portion 15 passes through the approximate center portion of the dark part region in the acquired image data in the processing in the flowchart in FIG. 2.

The arithmetic processing section 91 calculates the amount of bending and the bending direction of the bending portion 16 such that the distal end portion 15 passes through the target position set in the step S6 in FIG. 2 (step S7 in FIG. 2).

The arithmetic processing section 91 performs arithmetic operation of the bending control information required for actually bending the bending portion 16, based on the amount of bending and the bending direction of the bending portion 16 calculated in the processing in step S7 in FIG. 2 (step S8 in FIG. 2). The arithmetic processing section 91 outputs the arithmetic operation result to the bending control section 5, and thereafter repeatedly performing a series of processing steps from the step S1 in FIG. 2.

Note that, when the bending portion 16 is composed of a plurality of bending pieces connected to one end side of the wire and configured to be capable of changing the bending state according to tension or relaxation of the wire caused by the rotational driving of the motors, for example, the above-described bending control information is assumed to be shown as information related to the angle of the pulleys connected to the motors and the driving voltages applied to the motors. In addition, when the bending portion 16 has an alternative configuration other than the above-described configuration, for example, the above-described bending control information is assumed to be shown as information according to the alternative configuration.

As described above, the endoscope system 1 according to the present embodiment is configured to be capable of controlling the endoscope bending portion such that the endoscope distal end portion passes through the approximate center portion (of the dark part) in the lumen, that is, the endoscope distal end portion passes through the clearly set passing target position, by performing each of the processing steps shown in FIG. 2 in the automatic bending mode. According to such a configuration, the endoscope system 1 according to the present embodiment can facilitate the insertion operation of the endoscope regardless of the knowledge or the experience of the person who actually operates the endoscope. Furthermore, the endoscope system 1 of the present embodiment enables smooth bending operation of the endoscope regardless of the knowledge or the experience of the person who actually performs the operation by performing the processing steps shown in FIG. 2 in the automatic bending mode.

In addition, the arithmetic processing section 91 may perform the processing shown in the flowcharts in FIG. 4 and FIG. 5 in the automatic bending mode, for example, instead of performing the processing shown in the flowchart in FIG. 2.

Now description will be made on the processing performed by the arithmetic processing section 91 for setting the target position as the passing target for the distal end portion 15, with reference to FIG. 4.

The arithmetic processing section 91 acquires image data based on the video signal inputted thereto (step S11 in FIG. 4), and thereafter performs distortion correction on the image data (step S12 in FIG. 4). According to such processing, the arithmetic processing section 91 acquires the image data in which a monochrome portion is eliminated from the original image based on the inputted video signal.

The arithmetic processing section 91 uses the method disclosed in Japanese Patent Application Laid-Open Publication No. 2-203831, for example, to detect the dark part region in the image data acquired in the processing in step S12 in FIG. 4 (step S13 in FIG. 4).

The arithmetic processing section 91 calculates the two-dimensional coordinates of the gravity center point of the dark part region based on the dark part region detected by the processing in step S13 in FIG. 4 (step S14 in FIG. 4).

After that, the arithmetic processing section 91 transforms the calculated two-dimensional coordinates of the gravity center point by the processing in step S14 in FIG. 4 into the target position given by the three-dimensional coordinates by using the Shape From Shading method and the like (step S15 in FIG. 4), for example, and thereafter repeats a series of processing steps from step S11 in FIG. 4 again.

That is, the arithmetic processing section 91 sets the three-dimensional position to be the target such that the distal end portion passes through the approximate center portion of the dark part region in the acquired image data in the processing in the flowchart in FIG. 4. The target position given by the three-dimensional coordinates which is acquired by the processing in FIG. 4 is appropriately updated according to the case where the distal end portion 15 has passed through the target position or the case where the shape of the dark part region has changed, for example.

In addition, the arithmetic processing section 91 performs the processing shown in the flowchart in FIG. 5 in parallel with the processing shown in the flowchart in FIG. 4.

Now, description will be made on the processing performed by the arithmetic processing section 91 for setting the content of the control performed on the bending portion 16, with reference to FIGS. 5 and 6.

The arithmetic processing section 91 calculates the current position and direction of the distal end portion 15 based on the three-dimensional coordinate information outputted from the source coil position/orientation detecting section 46 (step S21 in FIG. 5).

After that, the arithmetic processing section 91 determines in the processing in FIG. 4 whether or not the target position given by the three-dimensional coordinates is updated (step S22 in FIG. 5). When detecting by the processing in FIG. 4 that the target position given by the three-dimensional coordinates has been updated, the arithmetic processing section 91 performs processing for calculating an interpolation curve used for estimating a path of the distal end portion 15 corresponding to the updated target position (step S23 in FIG. 5). In addition, when detecting by the processing in FIG. 4 that the target position given by the three-dimensional coordinates has not been updated, the arithmetic processing section 91 performs the processing in step S24 in FIG. 5 to be described later, while retaining the target position and the interpolation curve directed toward the target position.

In the processing in step S23 in FIG. 5, first the arithmetic processing section 91 acquires the three-dimensional coordinate positions of a plurality of source coils including at least one or more source coils provided in the bending portion 16, based on the three-dimensional coordinate information outputted from the source coil position/orientation detecting section 46. Specifically, as shown in FIG. 6, for example, the arithmetic processing section 91 acquires three three-dimensional coordinate positions including the three-dimensional coordinate position of a source coil $C_1$ provided in the distal end portion 15 and the three-dimensional coordinate positions of the source coils $C_2$ and $C_3$ provided in the bending portion 16, based on the three-dimensional coordinate information outputted from the source coil position/orientation detecting section 46.

In the processing in step S23 in FIG. 5, next the arithmetic processing section 91 calculates a parametric curve by applying the Catmull Rom curve equation to the above-described three three-dimensional coordinate positions and the target position given by the three-dimensional coordinates updated in the processing in FIG. 4.

Then, the arithmetic processing section 91 calculates the parametric curve as the interpolation curve which is the processing result in step S23 in FIG. 5. According to the calculation, the arithmetic processing section 91 sets a curve Id connecting the source coils $C_1$, $C_2$ and $C_3$, and a target position D given by the three-dimensional coordinates, as the interpolation curve used for estimating the path of the distal end portion 15, as shown in FIG. 6, for example.

That is, the arithmetic processing section 91 as a path estimating section estimates the interpolation curve calculated by the processing in step S23 in FIG. 5, as the path through which the distal end portion 15 is to be passed.

Note that the arithmetic processing section 91 of the present embodiment is not limited to one which sets the above-described interpolation curve by using the three-dimensional coordinate positions of the source coils $C_1$, $C_2$ and $C_3$. Specifically, the arithmetic processing section 91 of the present embodiment may perform arithmetic operation for setting the above-described interpolation curve by using the three-dimensional coordinate position of any of the source coils, as long as the three-dimensional coordinate positions of a plurality of source coils including at least one or more source coils provided in the bending portion 16.

Meanwhile, the arithmetic processing section 91 calculates a moving velocity of the source coil $C_1$ per unit time, for example, based on the three-dimensional coordinate information outputted from the source coil position/orientation detecting section 46, thereby calculating the moving distance L of the distal end portion 15 after Δt seconds (step S24 in FIG. 5).

The arithmetic processing section 91 calculates the bending control target position based on the curve Id and the moving distance L (step S25 in FIG. 5).

That is, in the processing in step S25 in FIG. 5, the arithmetic processing section 91 calculates the above-described vector Vd and sets a position where a point P, which is a point on the curve Id and is an end point of the vector Vd, exists.

The arithmetic processing section 91 calculates the amount of bending and the bending direction of the bending portion 16 such that the distal end portion 15 moves toward the bending control target position set in the step S25 in FIG. 5 (step S26 in FIG. 5)

The arithmetic processing section 91 performs arithmetic operation of the bending control information required for actually bending the bending portion 16, based on the amount of bending and the bending direction of the bending portion 16 calculated in the processing in step S26 in FIG. 5 (step S27 in FIG. 5). The arithmetic processing section 91 outputs the arithmetic operation result to the bending control section 5, and thereafter repeatedly performing a series of processing steps from the step S21 in FIG. 5.

As described above, the endoscope system 1 according to the present embodiment is configured to perform each of the processing steps shown in FIG. 4 and FIG. 5 in the automatic bending mode, thereby capable of controlling the endoscope bending portion such that the endoscope distal end portion passes through the approximate center portion (of the dark part) in the lumen while bending the endoscope bending portion relatively gently. According to such a configuration, the endoscope system 1 of the present embodiment can facilitate the insertion operation of the endoscope regardless of the knowledge or the experience of the person who actually operates the endoscope. Furthermore, the endoscope system 1 according to the present embodiment performs the processing steps shown in FIG. 4 and FIG. 5 in the automatic bending mode, thereby capable of smoothly performing the bending operation of the endoscope regardless of the knowledge or the experience of the person who actually operates the endoscope.

(Second Embodiment)

Note that detailed descriptions will be properly omitted below regarding the components which have the same configurations as those in the first embodiment and perform the same processing as that in the first embodiment.

Figure 7:
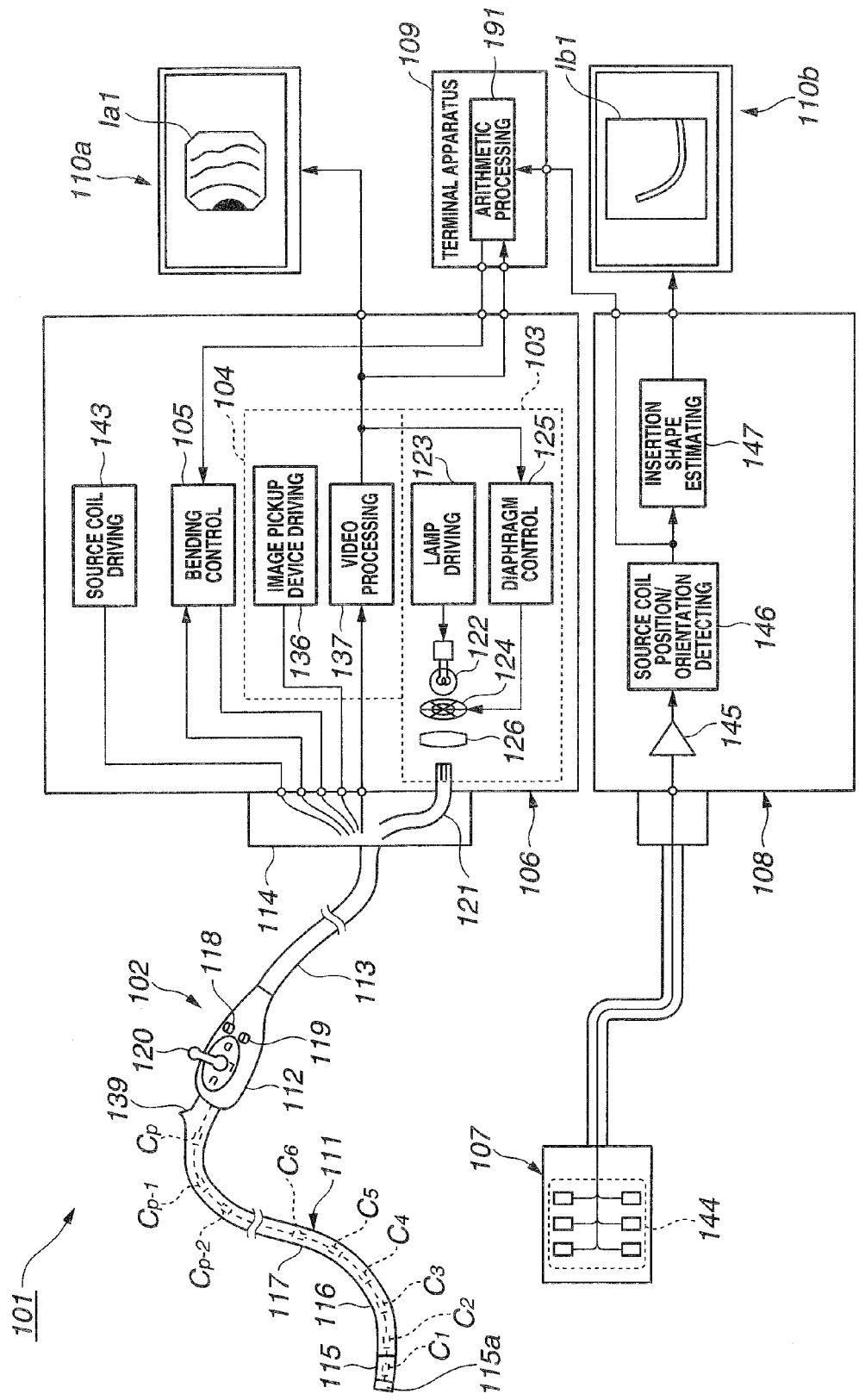
FIG. 7 is a view showing a configurational example of a main part of an endoscope system according to a second embodiment of the present invention.
Figure 8:
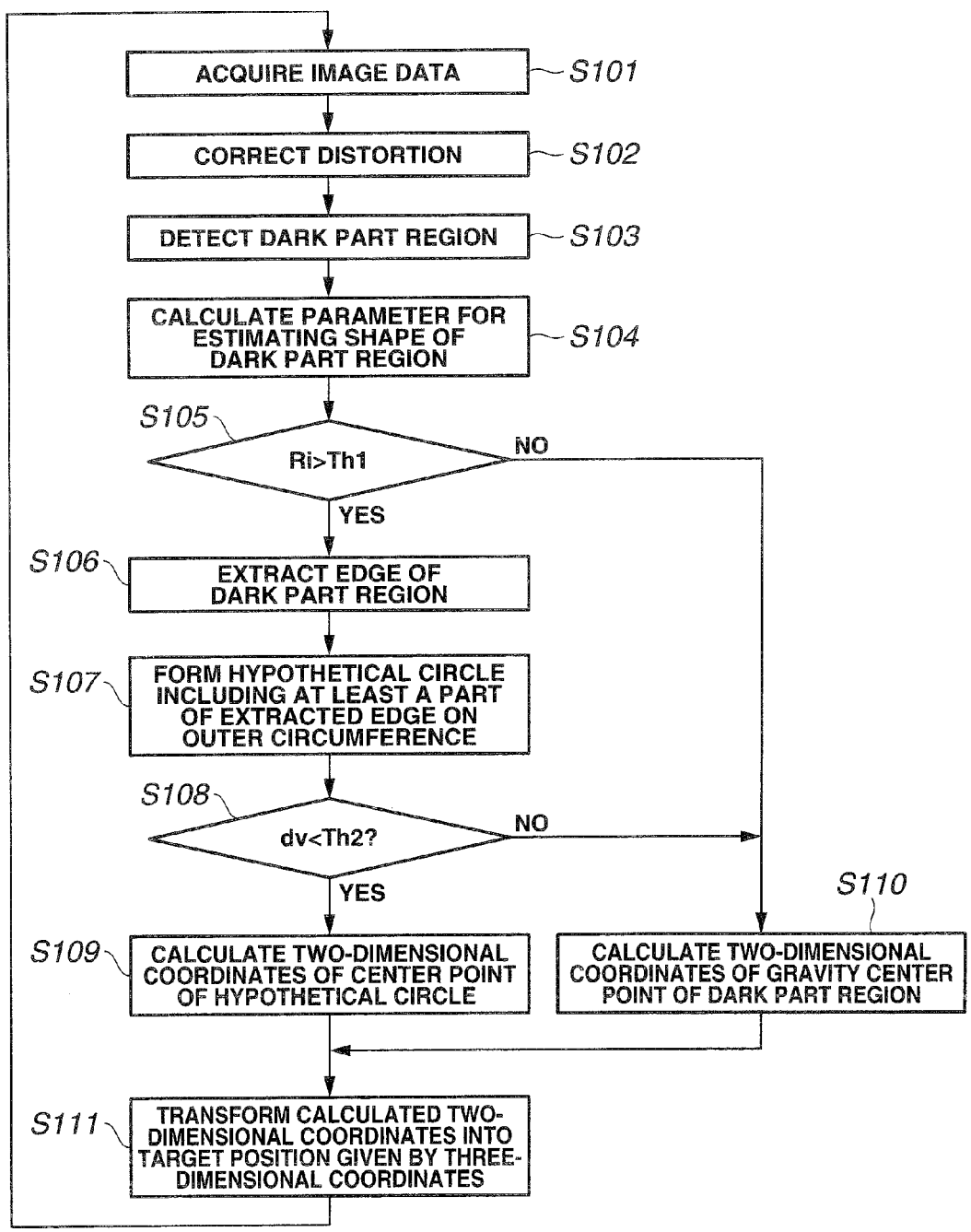
FIG. 8 is a flowchart showing an example of target position detecting processing performed in a terminal apparatus in FIG. 7.
Figure 9:
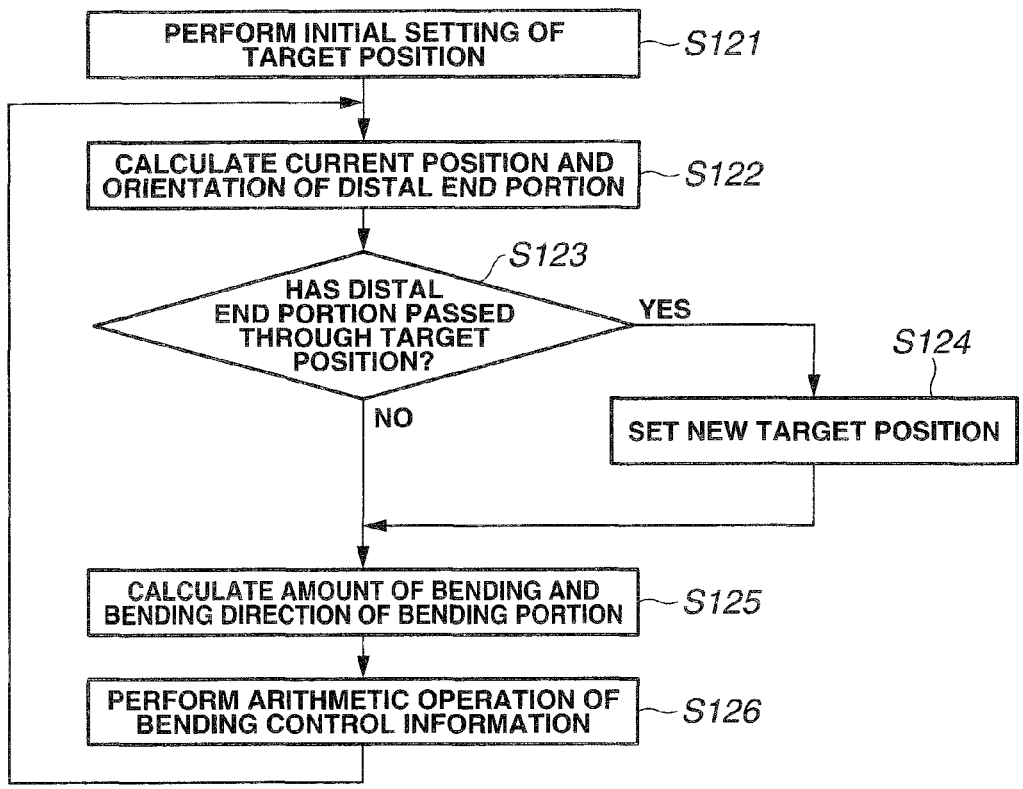
FIG. 9 is a flowchart showing an example of bending control setting processing performed in the terminal apparatus in FIG. 7.
Figure 10:
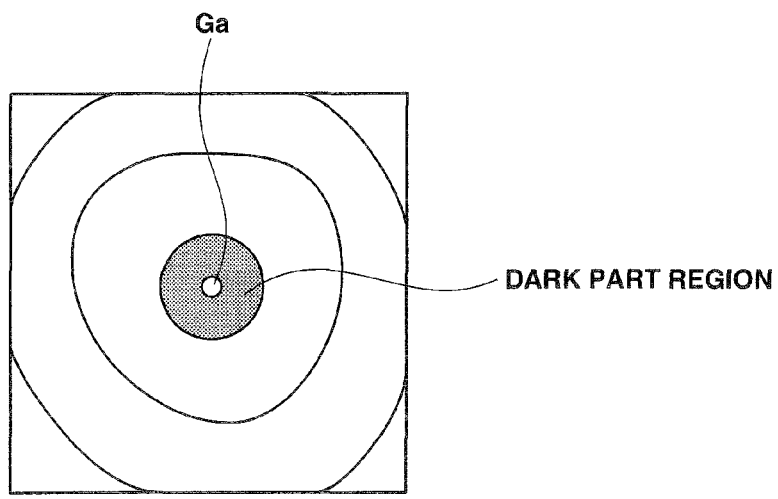
FIG. 10 is a view showing an example of a dark part region existing in image data.
Figure 11:
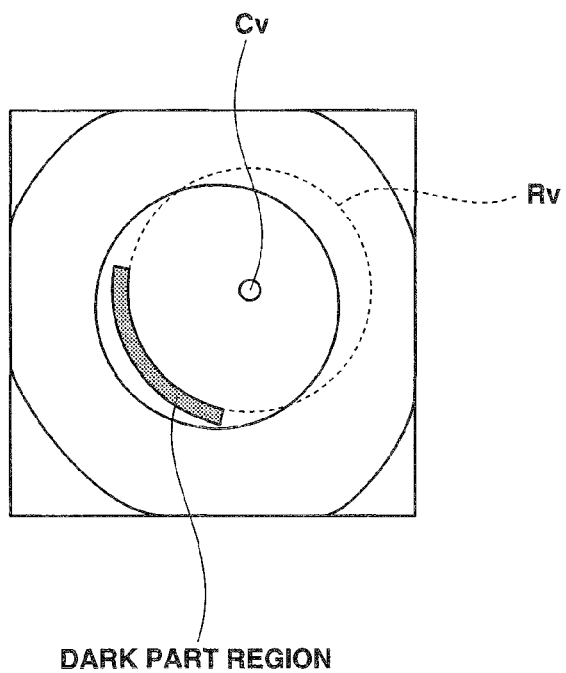
FIG. 11 is a view showing an example of a dark part region existing in the image data, which is different from the example in FIG. 10.
Figure 12:
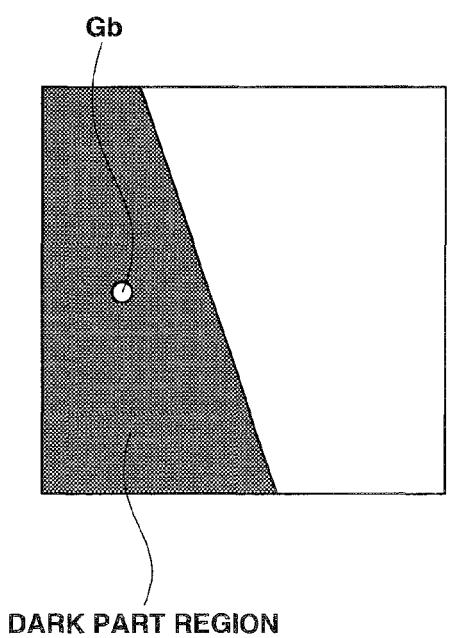
FIG. 12 is a view showing an example of a dark part region existing in the image data, which is different from the examples in FIG. 10 and FIG. 11.

FIGS. 7 to 12 relate to an embodiment of the present invention. FIG. 7 is a view showing a configurational example of a main part of an endoscope system according to an embodiment of the present invention. FIG. 8 is a flowchart showing an example of target position detecting processing performed in a terminal apparatus in FIG. 7. FIG. 9 is a flowchart showing an example of bending control setting processing performed in the terminal apparatus in FIG. 7. FIG. 10 is a view showing an example of a dark part region existing in image data. FIG. 11 is a view showing an example of a dark part region existing in the image data, which is different from the example in FIG. 10. FIG. 12 is a view showing an example of a dark part region existing in the image data, which is different from the examples in FIG. 10 and FIG. 11.

As shown in FIG. 7, an endoscope system 101 according to the present embodiment of the present invention includes: an endoscope 102 which is configured to be inserted into a body cavity of a patient as a subject and which picks up an image of a photographic subject in the body cavity; a processor 106 to and from which a connector 114 provided in the endoscope 102 is attachable and detachable; a sense coil unit 107 arranged around a bed on which the patient lies; an endoscope insertion shape detecting apparatus 108; a terminal apparatus 109; a monitor 110a, and a monitor 110b.

In addition, the processor 106 includes: a light source section 103 that supplies illumination light for illuminating a photographic subject as an image pickup object to the endoscope 102; a signal processing section 104 that generates a video signal by performing signal processing on an image pickup signal outputted from the endoscope 102 and outputs the generated video signal; a bending control section 105 that performs bending control on the endoscope 102; and a source coil driving section 143.

The endoscope 102 includes: an elongated insertion portion 111 to be inserted in the subject; an operation portion 112 provided at a rear end of the insertion portion 111; and a universal cord 113 extended from the operation portion 112. The connector 114 that is attachable to and detachable from the processor 106 is provided at a rear end of the universal cord 113.

The insertion portion 111 includes: a rigid distal end portion 115 provided on a distal end side; a bending portion 116 connected to a rear end of the distal end portion 115; and a flexible tube portion 117 having flexibility that is provided between a rear end of the bending portion 116 and a front end of the operation portion 112. Furthermore, p-pieces of source coils $C_1$, $C_2$, . . . , and $C_p$ that generate magnetic fields corresponding to the source coil driving signals applied by the source coil driving section 143 are provided in the insertion portion 111 at substantially equal intervals.

The distal end portion 115 is provided with an image pickup section 115a including an objective optical system that forms an image of a photographic subject and an image pickup device that outputs the image of the photographic subject formed through the objective optical system as an image pickup signal.

The operation portion 112 is provided with a scope switch 118 that gives an instruction for acquiring a freeze image (still image), for example; a bending mode switching switch 119 that gives an instruction for switching the bending mode of the bending portion 116 to either the manual bending mode or the automatic bending mode, and a joystick 120 for bending operation for instructing the bending direction and the bending angle of the bending portion 116 when the manual bending mode is selected. In addition, at a portion which is on a rear end side of the flexible tube portion 117 and near the front end of the operation portion 112 is provided a treatment instrument insertion port 139 leading to a channel for treatment instrument, not shown, through which a treatment instrument or the like is insertable.

A light guide 121 that transmits the illumination light supplied from the light source section 103 to the distal end portion 115 is inserted in the insertion portion 111 and the like of the endoscope 102.

One end surface (incident end surface) of the light guide 121 is arranged protruding from the connector 114. Furthermore, the other end surface (light-emitting end surface) of the light guide 121 is arranged in the vicinity of an illumination optical system, not shown, provided in the distal end portion 115. According to such a configuration, in a state where the connector 114 is connected to the processor 106, the illumination light supplied from the light source section 103 passes through the light guide 121 and the illumination optical system, not shown, and thereafter illuminates the photographic subject as the image pickup object of the image pickup section 115a.

The light source section 103 includes: a lamp 122 that emits illumination light which is white light, for example; a lamp driving section 123 that supplies a power source required for driving the lamp 122; a diaphragm 124; a diaphragm control section 125 that increases and decreases the diaphragm amount (opening amount) of the diaphragm 124 based on the video signal outputted from the signal processing section 104; and a light condensing optical system 126 that condenses the illumination light passed through the diaphragm 124 and supplies the illumination light to the incident end surface of the light guide 121.

The diaphragm control section 125, for example, calculates the average brightness based on the luminance components of the inputted video signal, and thereafter appropriately changes the light amount of the illumination light passing through the diaphragm 124 by increasing or decreasing the diaphragm amount (opening amount) of the diaphragm 124 based on a difference value which is a value obtained by subtracting a reference value corresponding to the appropriate brightness from the average brightness.

The signal processing section 104 includes an image pickup device driving section 136 that outputs an image pickup device driving signal for driving the image pickup device provided in the image pickup section 115a, and a video processing section 137 that generates a video signal by performing signal processing on the image pickup signal outputted from the image pickup section 115a and outputs the generated video signal. According to this configuration, an endoscopic image Ia1 based on the video signal is displayed on the monitor 110a.

When the bending mode of the bending portion 116 is switched to the manual bending mode based on the instruction given by the bending mode switching switch 119, the bending control section 105 performs control to change the bending direction and the bending angle of the bending portion 116 based on the inclination direction and the inclination amount of the joystick 120 for bending operation. In addition, when the bending mode of the bending portion 116 is switched to the automatic bending mode based on the instruction given by the bending mode switching switch 119, the bending control section 105 performs control to change the bending direction and the bending angle of the bending portion 116 based on the arithmetic operation result from the terminal apparatus 109.

The source coil driving section 143 is connected to the p-pieces of source coils $C_1, C_2, \ldots,$ and $C_p$ provided in the insertion portion 111, and sequentially applies an alternate current source coil driving signal to each of the source coils. As a result, an alternate current magnetic field is generated around each of the source coils provided in the insertion portion 111.

The sense coil unit 107 is provided with a sense coil group 144 that detects the magnetic field generated from each of the p-pieces of source coils $C_1, C_2, \ldots,$ and $C_p$ provided in the insertion portion 111 and outputs the detected magnetic fields as magnetic field detection signals.

The endoscope insertion shape detecting apparatus 108 having a function as a position detecting section includes: an amplifier 145 that amplifies the magnetic field detection signals outputted from the sense coil unit 107; a source coil position/orientation detecting section 146 that detects three-dimensional coordinate positions and orientations of the p-pieces of source coils $C_1, C_2, \ldots,$ and $C_p$ based on the magnetic field detection signals outputted from the amplifier 145, and outputs the detected three-dimensional coordinate positions and orientations as three-dimensional coordinate information; and an insertion shape estimating section 147 that estimates the insertion shape of the insertion portion 111 based on the three-dimensional coordinate information outputted from the source coil position/orientation detecting section 146, and outputs the estimated insertion shape as an insertion shape image signal. According to this configuration, an insertion shape image Ib1 of the insertion portion 111 based on the insertion shape image signal is displayed on the monitor 110b.

The terminal apparatus 109 includes an arithmetic processing section 191 composed of a CPU and the like. The arithmetic processing section 191 performs arithmetic operation related to the bending control performed when the bending mode of the bending portion 116 is the automatic bending mode, based on the video signal outputted from the video processing section 137 and the three-dimensional coordinate information outputted from the source coil position/orientation detecting section 146, and outputs the arithmetic operation result to the bending control section 105. Note that the specific content of the arithmetic operation performed in the arithmetic processing section 191 will be described later.

Next, description will be made on the working of the endoscope system 101. Note that description on the control in the case where the bending mode switching switch 119 is switched to the manual bending mode will be omitted below, and description will be mainly made on the control in the case where the bending mode switching switch 119 is switched to the automatic bending mode.

First, an operator connects and activates each of the parts of the endoscope system 101, and thereafter inserts the insertion portion 111 of the endoscope 102 into a body cavity of a patient and switches the bending mode switching switch 119 to the automatic bending mode. In response to the switching, the image pickup section 115a in the endoscope 102 starts picking up an image of a photographic subject, and the source coils provided in the insertion portion 111 start to generate magnetic fields.

The image pickup signal outputted from the image pickup section 115a in association with the image pickup of the photographic subject is outputted to the processor 106, through the universal cord 113 and the connector 114, to be converted into a video signal in the video processing section 137, and thereafter inputted to the arithmetic processing section 191 in the terminal apparatus 109. In addition, the magnetic field detection signals outputted from the sense coil unit 107 in association with the generation of magnetic fields from the source coils provided in the insertion portion 111 are amplified by the amplifier 145, to be converted as the three-dimensional coordinate information of the source coils by the source coil position/orientation detecting section 146, and thereafter inputted to the arithmetic processing section 191 in the terminal apparatus 109.

The arithmetic processing section 191 in the terminal apparatus 109 performs target position detecting processing based on the inputted video signal, thereby acquiring the three-dimensional coordinate position as a passing target for the distal end portion 115.

Here, the target position detecting processing performed by the arithmetic processing section 191 will be described.

The arithmetic processing section 191 in the terminal apparatus 109 acquires image data based on the inputted video signal (step S101 in FIG. 8), and thereafter performs distortion correction on the image data (step S102 in FIG. 8). By performing the processing steps described above, the arithmetic processing section 191 acquires image data in which a monochrome portion is eliminated from the original image based on the inputted video signal.

The arithmetic processing section 191 as a dark part region detecting section uses the method disclosed in Japanese Patent Application Laid-Open Publication No. 2-203831, for example, to detect the dark part region in the image data acquired by the processing in step S102 in FIG. 8 (step S103 in FIG. 8). Note that the arithmetic processing section 191 may use other method as the method of detecting the dark part region in an image, instead of the method disclosed in Japanese Patent Application Laid-Open Publication No. 2-203831.

After that, the arithmetic processing section 191 calculates a parameter for estimating the shape of the dark part region detected by the processing in the step S103 in FIG. 8 (step S104 in FIG. 8). Specifically, the arithmetic processing section 191 performs arithmetic operation using the following expressions (1) and (2) which are based on a primary moment m11 of the dark part region, a secondary moment m02 of the dark part region, and a secondary moment m20 of the dark part region, for example, and calculates a value of a ratio Ri between the major axis direction and minor axis direction in a case where an applicable ellipse is applied to the dark part region, as the parameter for estimating the shape of the dark part region.

$$msq = ((m20-m02) \times (m20-m02) + 4 \times m11 \times m11)^{1/2} \quad (1)$$

$$Ri = (((m20+m02)-msq)/((m20+m02)+msq))^{1/2} \quad (2)$$

The arithmetic processing section 191 determines whether or not the value of the ratio Ri calculated by the processing in step S104 in FIG. 8 is larger than a predetermined threshold Th1 (step S105 in FIG. 8).

When detecting that the value of the ratio Ri is equal to or smaller than the predetermined threshold Th1, the arithmetic processing section 191 estimates that the dark part region detected by the processing in the step S103 in FIG. 8 has the substantially circular shape as shown in FIG. 10, for example, and thereafter calculates the two-dimensional coordinates of a gravity center point Ga of the dark part region (step S110 in FIG. 8). Note that, as the processing for calculating the two-dimensional coordinates of the gravity center point of the dark part region, the arithmetic processing section 191 may perform the processing by regarding a centroid calculated according to sequence of points existing on the edge of the dark part region as the gravity center point, or may calculate the gravity center point using a 0th moment and the primary moment of the dark part region.

When detecting that the value of the ratio Ri is larger than the predetermined threshold Th1, the arithmetic processing section 191 judges that the dark part region detected by the processing in step S103 in FIG. 8 has another shape different from the substantially circular shape, and thereafter extracts the edge of the dark part region (step S106 in FIG. 8). Specifically, the arithmetic processing section 191 reduces the image data, and thereafter applies any one of Canny, Sobel, and Laplacian algorithms to the reduced image data to extract the edge of the dark part region.

Based on the edge of the dark part region extracted by the processing in the step S106 in FIG. 8, the arithmetic processing section 191 forms a hypothetical circle including at least a part of the edge on an outer circumference thereof (step S107 in FIG. 8). Note that, as the processing for forming the hypothetical circle, the arithmetic processing section 191 may perform processing based on a circle Hough transform, or processing to be described below.

The arithmetic processing section 191 detects shading gradient directions of the points on the edge of the dark part region, and after that, decides an approximate existing range of the center point of the hypothetical circle based on each of the shading gradient directions. Furthermore, the arithmetic processing section 191 calculates the distances from one point within the existing range to the respective points on the edge of the dark part region, and defines the summation of the distances as an evaluated value of the one point. The arithmetic processing section 191 calculates the evaluated values of all the points within the existing range and compares the values one another, thereby forming the hypothetical circle with the point whose evaluated value is the smallest as the center point and with the length from the center point to the edge of the dark part region as the radius.

The arithmetic processing section 191 determines whether or not the diameter dv of the hypothetical circle formed by the processing in step S107 in FIG. 8 is smaller than a predetermined threshold Th2 (step S108 in FIG. 8). Note that the threshold Th2 is assumed to be a value calculated based on the size of the image data acquired in the step S102 in FIG. 8, a diameter size of a normal lumen, or the data acquired in the past in substantially the same region of the same patient, for example.

When detecting that the diameter dv of the hypothetical circle is smaller than the predetermined threshold Th2, the arithmetic processing section 191 calculates the two-dimensional coordinates of the center point of the hypothetical circle (step S109 in FIG. 8). Specifically, the arithmetic processing section 191 calculates the two-dimensional coordinates of the center point Cv of the hypothetical circle Rv including on the outer circumference thereof at least a part of the edge of the dark part region, in the image data including the dark part region having a curved shape, as shown in FIG. 11, for example.

In addition, when detecting that the diameter dv of the hypothetical circle is equal to or larger than the predetermined threshold Th2, the arithmetic processing section 191 calculates the two-dimensional coordinates of the gravity center point of the dark part region (step S110 in FIG. 8). Specifically, the arithmetic processing section 191 calculates the two-dimensional coordinates of the gravity center point Gb of the dark part region in the image data including the dark part region having a shape which is neither the substantially circular shape nor the curved shape, as shown in FIG. 12, for example.

After that, the arithmetic processing section 191 as a target position setting section transforms the two-dimensional coordinates of any one of the center point Cv, the gravity center point Ga, and the gravity center point Gb calculated by the processing up to the step S110 in FIG. 8 into the target position given by the three-dimensional coordinates by using the Shape From Shading method and the like (step S111 in FIG. 8), and thereafter repeats the series of processing steps from the step S101 again.

That is, when detecting the existence of the dark part region having the substantially circular shape as shown in FIG. 10, for example, by the above-described target position detecting processing, the arithmetic processing section 191 regards that the dark part region is generated by the lumen, and sets the three-dimensional coordinate position as the target such that the distal end portion 115 passes through the approximate center portion of the lumen.

Furthermore, when detecting the existence of the dark part region having the curved shape as shown in FIG. 11, for example, by the above-described target position detecting processing, the arithmetic processing section 191 regards that the dark part region is generated by the folds and the like of the wall surface of the lumen and sets the three-dimensional coordinate position as the target such that the distal end portion 115 is prevented from moving to the wall surface side and the distal end portion 115 passes through the position in the lumen where the distal end portion 115 is supposed to pass.

Meanwhile, the arithmetic processing section 191 performs a bending control setting processing for setting the content of control with respect to the bending portion 116 in the automatic bending mode, in parallel with the above-described target position detecting processing.

Now, description will be made on the bending control setting processing performed by the arithmetic processing section 191.

The arithmetic processing section 191 performs the above-described target position detecting processing for performing the initial setting of the target position for the distal end portion 115 to be passed at the timing immediately after the bending mode switching switch 119 is switched to the automatic bending mode (step S121 in FIG. 9).

In addition, the arithmetic processing section 191 calculates the current position and orientation of the distal end portion 115 based on the three-dimensional coordinate information outputted from the source coil position/orientation detecting section 146 (step S122 in FIG. 9).

After that, the arithmetic processing section 191 compares the current position and orientation of the distal end portion 115 calculated in the processing in the step S122 in FIG. 9 with the target position for the distal end portion 115 to be passed, thereby determining whether or not the distal end portion 115 has passed through the target position (step S123 in FIG. 9).

When detecting that the distal end portion 115 has passed through the target position, the arithmetic processing section 191 performs the above-described target position detecting processing again in order to set a new target position (step S124 in FIG. 9). In addition, when detecting that the distal end portion 115 has not passed through the target position, the arithmetic processing section 191 retains the target position and continues the processing.

After performing the processing in the step S123 or the step S124 in FIG. 9, the arithmetic processing section 191 calculates the amount of bending and the bending direction of the bending portion 116 such that the distal end portion 115 passes through the set target position (step S125 in FIG. 9). Note that, in the present embodiment, the arithmetic processing section 191 may calculate the amount of bending and the bending direction of the bending portion 116 by using different calculation methods depending on the shapes (substantially circular shape, curved shape or other shape) of the dark part region detected by the above-described target position detecting processing.

The arithmetic processing section 191, as a bending control information calculating section, performs arithmetic operation of the bending control information required for actually bending the bending portion 116, based on the amount of bending and the bending direction of the bending portion 116 calculated in the processing in the step S125 in FIG. 9 (step S126 in FIG. 9), and outputs the arithmetic operation result to the bending control section 105. After that, the arithmetic processing section 191 repeatedly performs a series of processing steps from the step S122 in FIG. 9 again.

Note that, when the bending portion 116 is composed of a plurality of bending pieces connected to one end side of the wire and configured to be capable of changing the bending state thereof according to tension or relaxation of the wire caused by the rotational driving of the motors, for example, the above-described bending control information is assumed to be shown as information related to the angles of the pulleys connected to the motors and the driving voltages applied to the motors. In addition, when the bending portion 116 has an alternative configuration other than the above-described configuration, for example, the above-described bending control information is assumed to be shown as information according to the alternative configuration.

The bending control section 105 is capable of performing, in the automatic bending mode, a control with respect to the bending portion 116 such that the distal end portion 115 always passes through the target position set in the above-described target position detecting processing, based on the arithmetic operation result outputted from the arithmetic processing section 191 in the terminal apparatus 109.

As described above, the endoscope system 101 according to the present embodiment is configured to be capable of controlling the endoscope bending portion such that the position and the orientation of the endoscope distal end portion is located at a appropriate position and oriented in a appropriate direction according to the insertion operation of the endoscope insertion portion in the automatic bending mode. According to such a configuration, the endoscope system 101 according to the present embodiment can facilitate the insertion operation of the endoscope regardless of the knowledge or the experience of the person who actually operates the endoscope.

(Third Embodiment)

Note that detailed description will be properly omitted below regarding the components which have the same configuration as that in the first embodiment, and the components which performs the same processings as those in the first and the second embodiments.

Figure 13:
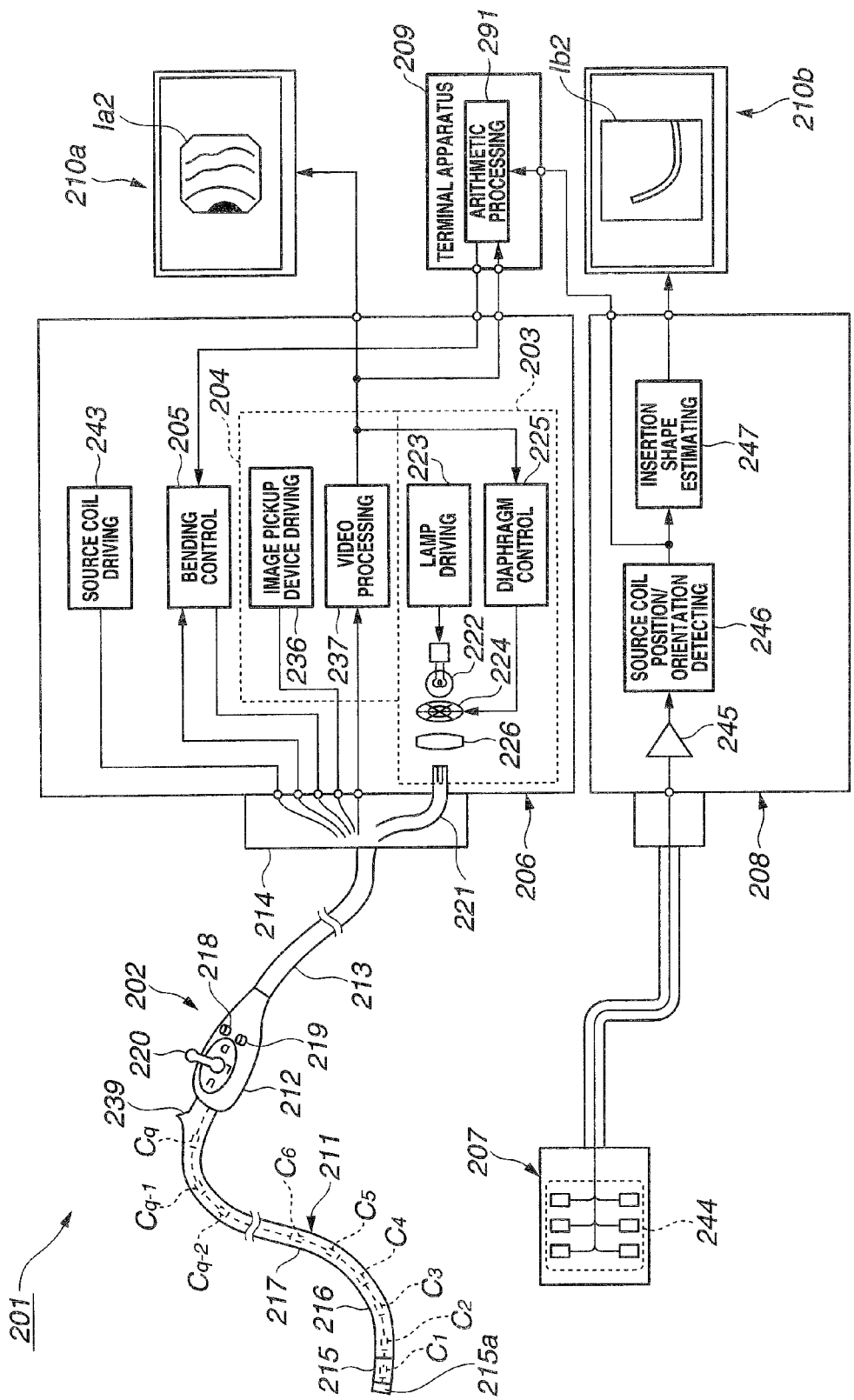
FIG. 13 is a view showing a configurational example of a main part of the endoscope system according to a third embodiment of the present invention.
Figure 14:
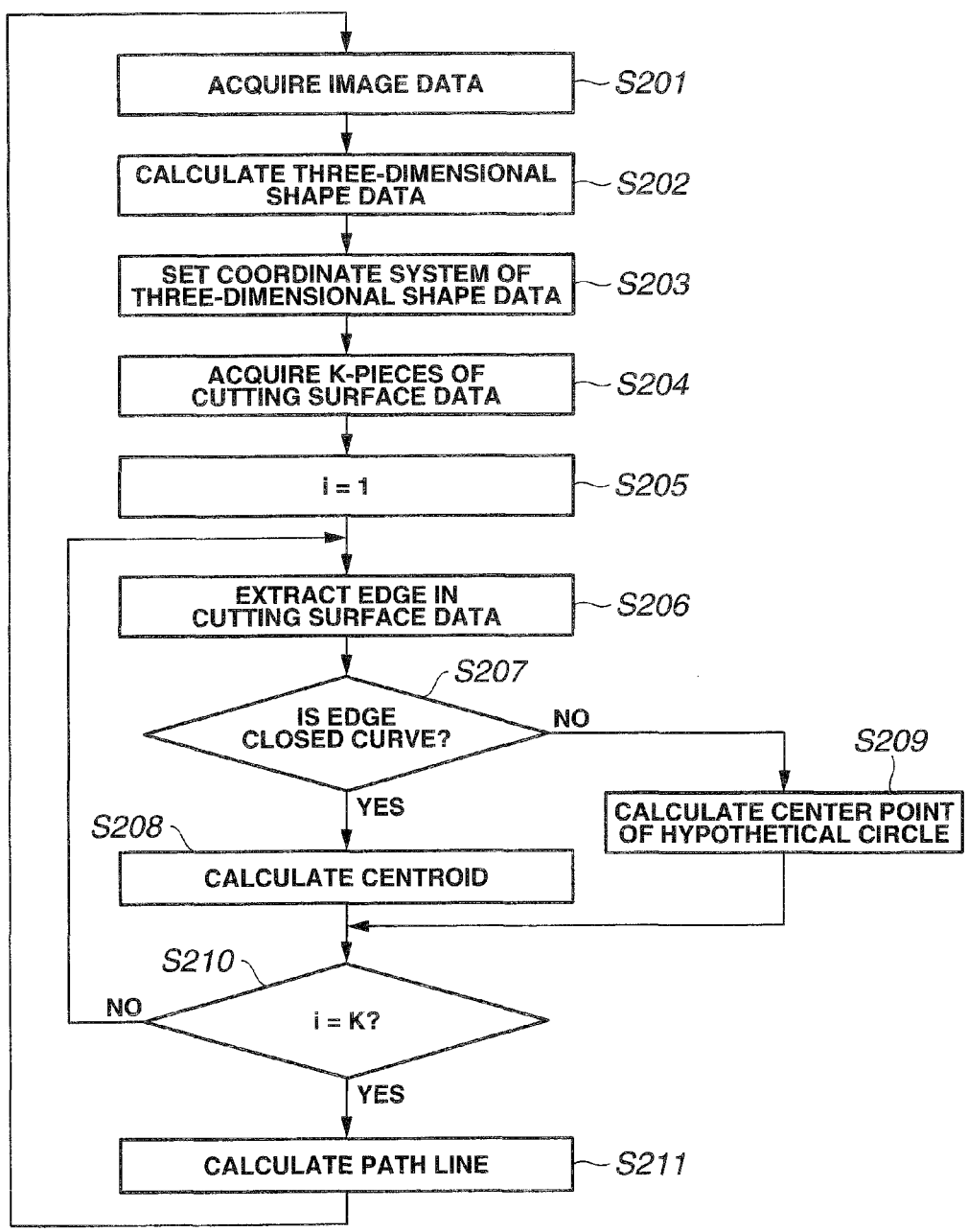
FIG. 14 is a flowchart showing an example of processing performed to set a path for the distal end portion to be passed.
Figure 15:
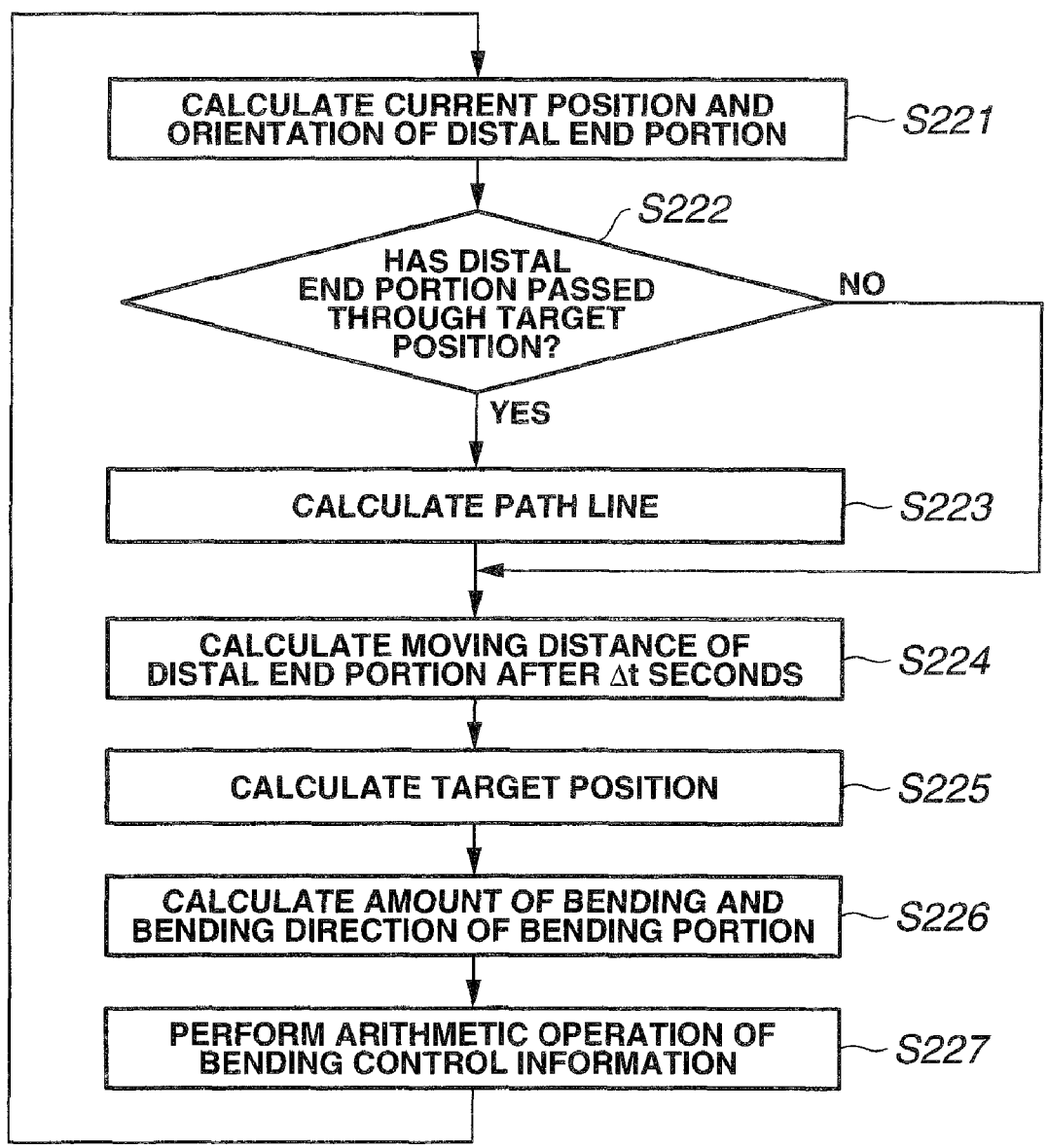
FIG. 15 is a flowchart showing an example of processing performed for setting a content of bending control with respect to the bending portion.
Figure 16:
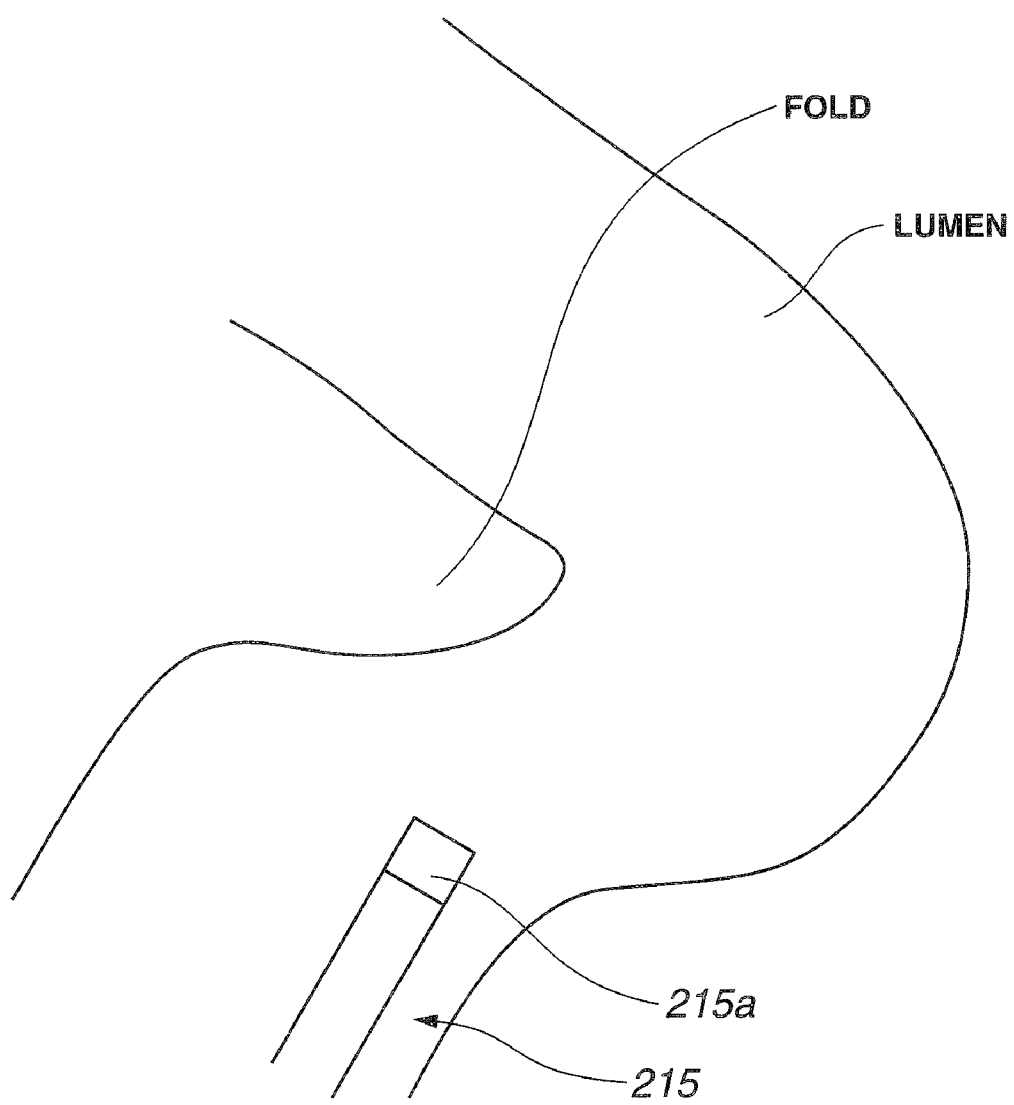
FIG. 16 is a view showing an example of a shape of a lumen in the vicinity of a current position of the distal end portion.
Figure 17:
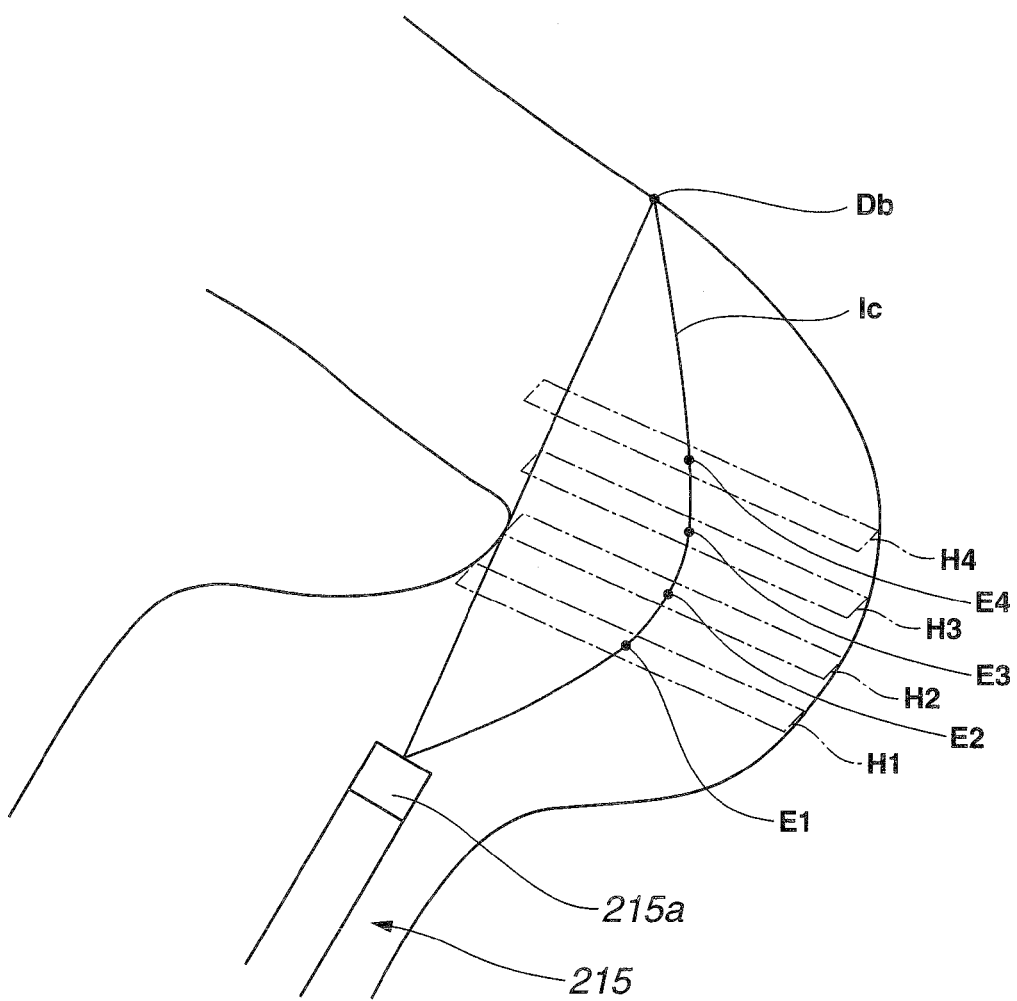
FIG. 17 is a schematic view showing a brief overview of the processing in the flowchart in FIG. 14.
Figure 18:
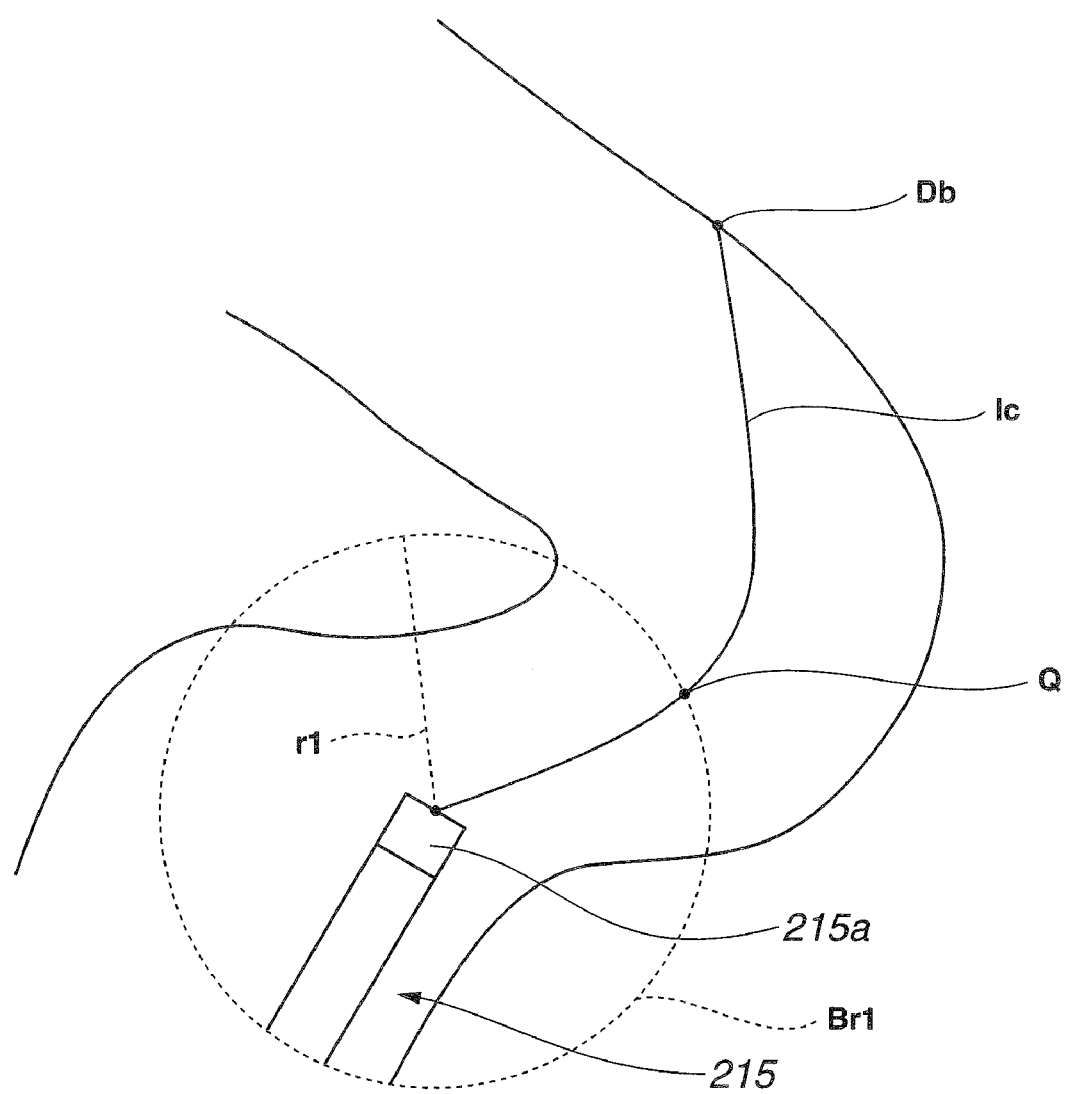
FIG. 18 is a view showing an example of processing for calculating the target position for the distal end portion to be passed.
Figure 19:
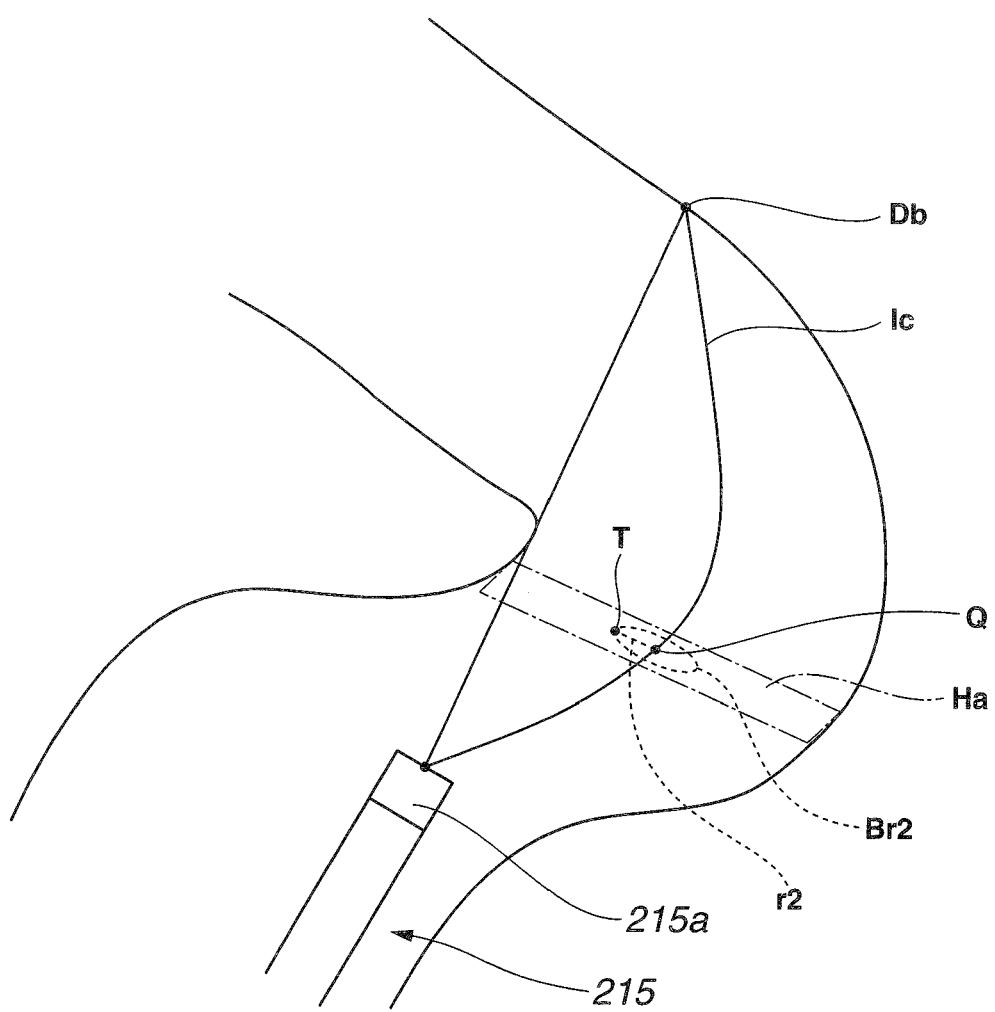
FIG. 19 is a view showing an example of the processing for calculating the target position for the distal end portion to be passed, which is different from the example in FIG. 18.
Figure 20:
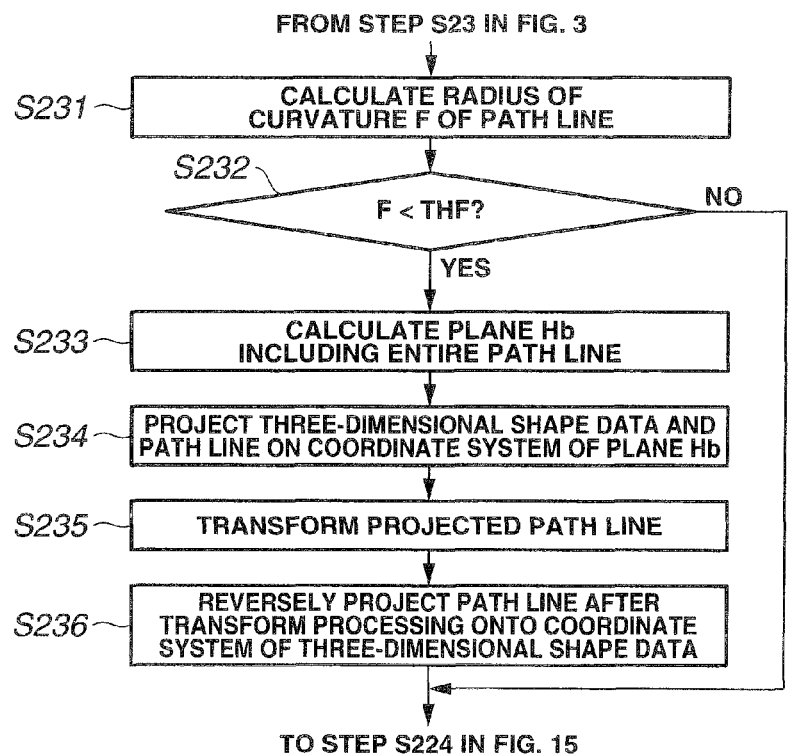
FIG. 20 is a view showing an example of processing which can be added to the flowchart in FIG. 15.
Figure 21:
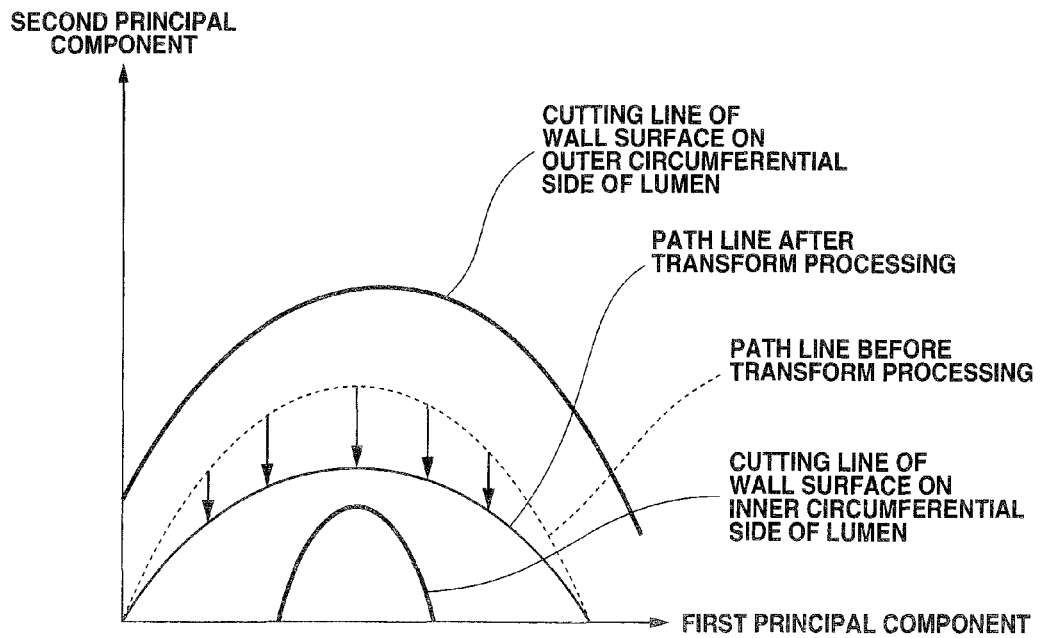
FIG. 21 is a schematic view showing the brief overview of the processing in the flowchart in FIG. 20.

FIGS. 13 to 21 relate to an embodiment of the present invention. FIG. 13 is a view showing a configurational example of a main part of an endoscope system according to the present embodiment of the present invention. FIG. 14 is a flowchart showing an example of processing for setting a path for the distal end portion to be passed. FIG. 15 is a flowchart showing an example of processing performed for setting a content of the bending control with respect to the bending portion. FIG. 16 is a view showing an example of a shape of a lumen in the vicinity of the current position of the distal end portion. FIG. 17 is a schematic view showing a brief overview of the processing shown in the flowchart in FIG. 14. FIG. 18 is a view showing an example of processing of calculating a target position for the distal end portion to be passed. FIG. 19 is a view showing an example of processing of calculating a target position for the distal end portion to be passed, which is different from the example shown in FIG. 18. FIG. 20 is a view showing an example of processing which can be added to the processing in the flowchart in FIG. 15. FIG. 21 is a schematic diagram showing a brief overview of the processing in the flowchart in FIG. 20.

As shown in FIG. 13, an endoscope system 201 according to the third embodiment of the present invention includes: an endoscope 202 which is configured to be inserted into a body cavity of a patient as a subject and which picks up an image of a photographic subject in the body cavity; a processor 206 to and from which a connector 214 provided in the endoscope 202 is attachable and detachable; a sense coil unit 207 arranged around a bed on which a patient lies; an endoscope insertion shape detecting apparatus 208; a terminal apparatus 209; a monitor 210a, and a monitor 210b.

In addition, the processor 206 includes: a light source section 203 that supplies illumination light for illuminating a photographic subject as an image pickup object to the endoscope 202; a signal processing section 204 that generates a video signal by performing signal processing on an image pickup signal outputted from the endoscope 202 and outputs the generated video signal; a bending control section 205 that performs bending control on the endoscope 202; and a source coil driving section 243.

The endoscope 202 includes an elongated insertion portion 211 to be inserted in the body cavity (lumen) of a subject; an operation portion 212 provided at a rear end of the insertion portion 211; and a universal cord 213 extended from the operation portion 212. The connector 214 that is attachable to and detachable from the processor 206 is provided at a rear end of the universal cord 213.

The insertion portion 211 includes: a rigid distal end portion 215 provided on a distal end side; a bending portion 216 connected to a rear end of the distal end portion 215; and a flexible tube portion 217 having flexibility that is provided between a rear end of the bending portion 216 and a front end of the operation portion 212. Furthermore, q-pieces of source coils $C_1, C_2, \ldots,$ and $C_q$ that generate magnetic fields corresponding to the source coil driving signals applied by the source coil driving section 243 are provided in the insertion portion 211 at substantially equal intervals.

The distal end portion 215 is provided with an image pickup section 215a including an objective optical system that forms an image of a photographic subject and an image pickup device that outputs the image of the photographic subject formed through the objective optical system as an image pickup signal.

The operation portion 212 is provided with a scope switch 218 that gives an instruction for acquiring a freeze image (still image), for example; a bending mode switching switch 219 that gives an instruction for switching the bending mode of the bending portion 216 to either the manual bending mode or the automatic bending mode; a joystick 220 for bending operation that gives instructions on the bending direction and the bending angle of the bending portion 216 when the manual bending mode is selected. In addition, at a portion on a rear end side of the flexible tube portion 217 and near the front end of the operation portion 212 is provided a treatment instrument insertion port 239 leading to a channel for treatment instrument, not shown, through which a treatment instrument and the like is insertable.

A light guide 221 that transmits the illumination light supplied from the light source section 203 to the distal end portion 215 is inserted in the insertion portion 211 and the like of the endoscope 202.

One end surface (incident end surface) of the light guide 221 is arranged protruding from the connector 214. Furthermore, the other end surface (light-emitting end surface) of the light guide 221 is arranged in the vicinity of an illumination optical system, not shown, provided in the distal end portion 215. According to such a configuration, in a state where the connector 214 is connected to the processor 206, the illumination light supplied from the light source section 203 passes through the light guide 221 and the illumination optical system, not shown, and thereafter illuminates the photographic subject as the image pickup object of the image pickup section 215a.

The light source section 203 includes: a lamp 222 that emits illumination light which is white light, for example; a lamp driving section 223 that supplies a power source required for driving the lamp 222; a diaphragm 224; a diaphragm control section 225 that increases and decreases the diaphragm amount (opening amount) of the diaphragm 224 based on the video signal outputted from the signal processing section 204; and a light condensing optical system 226 that condenses the illumination light passed through the diaphragm 224 and supplies the illumination light to the incident end surface of the light guide 221.

The diaphragm control section 225, for example, calculates the average brightness based on the luminance components of the inputted video signal, and appropriately changes the light amount of the illumination light passing through the diaphragm 224 by increasing or decreasing the diaphragm amount (opening amount) of the diaphragm 224 based on a difference value which is a value obtained by subtracting a reference value corresponding to the appropriate brightness from the average brightness.

The signal processing section 204 includes: an image pickup device driving section 236 that outputs an image pickup device driving signal for driving the image pickup device provided in the image pickup section 215a; and a video processing section 237 that generates a video signal by performing signal processing on the image pickup signal outputted from the image pickup section 215a and outputs the generated video signal. According to this configuration, an endoscopic image Ia2 according to the video signal is displayed on the monitor 210a.

When the bending mode of the bending portion 216 is switched to the manual bending mode based on the instruction given by the bending mode switching switch 219, the bending control section 205 performs control to change the bending direction and the bending angle of the bending portion 216 based on the inclination direction and the inclination amount of the joystick 220 for bending operation. In addition, when the bending mode of the bending portion 216 is switched to the automatic bending mode based on the instruction given by the bending mode switching switch 219, the bending control section 205 performs control to change the bending direction and the bending angle of the bending portion 216 based on the arithmetic operation result from the terminal apparatus 209.

The source coil driving section 243 is connected to the q-pieces of source coils $C_1, C_2, \ldots, C_q$ provided in the insertion portion 211, and sequentially applies an alternate current source coil driving signal to each of the source coils. As a result, an alternate current magnetic field is generated around each of the source coils provided in the insertion portion 211.

The sense coil unit 207 is provided with a sense coil group 244 that detects the magnetic field generated from each of the q-pieces of source coils $C_1, C_2, \ldots, C_q$ provided in the insertion portion 211 and outputs the magnetic fields as magnetic field detection signals.

The endoscope insertion shape detecting apparatus 208 includes: an amplifier 245 that amplifies the magnetic field detection signals outputted from the sense coil unit 207; a source coil position/orientation detecting section 246 that detects three-dimensional coordinate positions and orientations of the q-pieces of source coils $C_1, C_2, \ldots,$ and $C_q$ based on the magnetic field detection signals outputted from the amplifier 245, and outputs the detected three-dimensional coordinate positions and orientations as insertion shape information; and an insertion shape estimating section 247 that estimates the insertion shape of the insertion portion 211 based on the insertion shape information outputted from the source coil position/orientation detecting section 246, and outputs the estimated insertion shape as an insertion shape image signal. According to this configuration, an insertion shape image Ib2 of the insertion portion 211 according to the insertion shape image signal is displayed on the monitor 210b.

The terminal apparatus 209 includes an arithmetic processing section 291 that performs arithmetic operation related to the bending control performed in the case where the bending mode of the bending portion 216 is the automatic mode, based on the video signal outputted from the video processing section 237 and the insertion shape information outputted from the source coil position/orientation detecting section 246, and outputs the arithmetic operation result to the bending control section 205. Note that the specific content of the arithmetic operation performed in the arithmetic processing section 291 will be described later.

Next, the working of the endoscope system 201 will be described. Note that description on the control in the case where the bending mode switching switch 219 is switched to the manual bending mode will be omitted below, and description will be mainly made on the control in the case where the bending mode switching switch 219 is switched to the automatic bending mode.

First, an operator connects and activates each of the parts of the endoscope system 201, and thereafter inserts the insertion portion 211 of the endoscope 202 into the body cavity of a patient and switches the bending mode switching switch 219 to the automatic bending mode. In response to this, the image pickup section 215a in the endoscope 202 starts picking up an image of a photographic subject, and each of the source coils provided in the insertion portion 211 starts to generate a magnetic field.

The image pickup signal outputted from the image pickup section 215a in association with the image pickup of the photographic subject is outputted to the processor 206 through the universal cord 213 and the connector 214, to be converted into a video signal in the video processing section 237, and thereafter inputted to the arithmetic processing section 291 in the terminal apparatus 209. In addition, the magnetic field detection signals outputted from the sense coil unit 207 in association with the generation of magnetic fields from the source coils provided in the insertion portion 211 are amplified in the amplifier 245 to be converted as the three-dimensional coordinate information of the source coils by the source coil position/orientation detecting section 246, and thereafter inputted to the arithmetic processing section 291 in the terminal apparatus 209.

The arithmetic processing section 291 in the terminal apparatus 209 performs processing based on the inputted video signal and the inputted three-dimensional coordinate information of the source coils, thereby setting the path for the distal end portion 215 to be passed and setting the control content for bending the bending portion 216 such that the distal end portion 215 is advanced substantially along the path.

Now, description will be made on the processing performed by the arithmetic processing section 291 in order to set the path for the distal end portion 215 to be passed, with reference to FIG. 14 and the like.

The arithmetic processing section 291 acquires image data based on the inputted video signal (step S201 in FIG. 14), and thereafter performs distortion correction on the image data. By performing the processing described above, the arithmetic processing section 291 acquires two-dimensional image data in which a monochrome portion is eliminated from the original image based on the inputted video signal.

Next, the arithmetic processing section 291 having a function as a three-dimensional shape calculating section calculates, based on the two-dimensional image data acquired by the processing in the step S201 in FIG. 14, three-dimensional shape data as data showing the shape of the lumen in the vicinity of the current position of the distal end portion 215 by using the Shape From Shading method, for example (step S202 in FIG. 14). According to such processing, the arithmetic processing section 291 detects that the shape of the lumen in the vicinity of the current position of the distal end portion 215 has a flexed portion formed by the folds and the like in the body cavity, as shown in FIG. 16, for example.

Then, the arithmetic processing section 291 sets, for example, a local coordinate system with a predetermined position on the distal end surface of the distal end portion 215 as the origin, an axis corresponding to the left/right direction of the image data acquired by the processing in the step S201 in FIG. 14 as the x-axis, an axis corresponding to up/down direction of the image data as the y-axis, and an axis corresponding to the depth direction of the image data as the z-axis, with respect to the three-dimensional shape data calculated by the processing in the step S202 in FIG. 14 (step S203 in FIG. 14).

After that, the arithmetic processing section 291 having a function as a cutting surface acquiring section acquires, based on the image data acquired by the processing in the step S201 in FIG. 14 and the three-dimensional shape data calculated by the processing in the step S202 in FIG. 14, K-pieces of cutting surface data within the field of view range of the endoscope 202 (or in the vicinity of the position where the distal end portion 215 exists) (step S204 in FIG. 14).

In the processing in the step S204 in FIG. 14, first the arithmetic processing section 291 detects the position of the dark point (the darkest point) in the three-dimensional shape data, based on the image data acquired by the processing in the step S201 in FIG. 14 and the three-dimensional shape data calculated by the processing in the step S202 in FIG. 14. Specifically, the arithmetic processing section 291 detects the point Db shown in FIG. 17, for example, as the dark point (the darkest point).

In the processing in the step S204 in FIG. 14, next the arithmetic processing section 291 acquires K-pieces of cutting surface data by cutting the three-dimensional shape data using K-pieces of planes which are perpendicular to the vector pointing from a predetermined position of the distal end surface of the distal end portion 215 to the point Db and which are set at substantially equal intervals. Specifically, the arithmetic processing section 291 acquires four pieces of data of the planes H1, H2, H3 and H4 shown in FIG. 17, as cutting surface data, for example.

The arithmetic processing section 291 sets a variable i ($1 \leq I \leq K$), which corresponds to the number attached to each piece of the cutting surface data acquired by the processing in step S204 in FIG. 14, to 1 (step S205 in FIG. 14), and thereafter extracts the edge of the i-th cutting surface data (step S206 in FIG. 14). Specifically, the arithmetic processing section 291 reduces the cutting surface data, and thereafter extracts the edge of the cutting surface data by applying any one of the Canny, Sobel or Laplacian algorithms to the reduced cutting surface data.

The arithmetic processing section 291 determines whether or not the edge of the cutting surface data extracted by the processing in the step S206 in FIG. 14 is closed curve (step S207 in FIG. 14). When detecting that the edge of the cutting surface data extracted by the processing in the step S206 in FIG. 14 is closed curve, the arithmetic processing section 291 calculates the centroid of the cutting surface data (step S208 in FIG. 14). In addition, when detecting that the edge of the cutting surface data extracted by the processing in the step S206 in FIG. 14 is not closed curve, the arithmetic processing section 291 forms a hypothetical circle including at least a part of the edge on the outer circumference thereof by using the circle Hough transform and then calculates the center point of the hypothetical circle (step S209 in FIG. 14).

That is, the arithmetic processing section 291 performs the processing of extracting the cross-sectional shape of the cutting surface in the three-dimensional data of the lumen to detect a path point corresponding to the cross-sectional shape of each of the cutting surfaces, as the processing in the steps S206 to S209 in FIG. 14.

The arithmetic processing section 291 repeatedly performs the processing shown in the steps S206 to S209 in FIG. 14 until the variable i becomes equal to K (step S210 in FIG. 14). Among the K-pieces of cutting surface data, as for the cutting surface data subjected to the processing in the step S208 in FIG. 14, the centroid is calculated, and as for the cutting surface data subjected to the processing in the step S209 in FIG. 14, the center point of the hypothetical circle is calculated. Specifically, the arithmetic processing section 291 repeatedly performs the processing in the steps S206 to S209 in FIG. 14, thereby calculating the points E1, E2, E3, and E4 on the plane H1, H2, H3, and H4, respectively, as shown in FIG. 17, for example.

When the calculation of the centroid or the center point of the hypothetical circle in each of the K-pieces of cutting surface data is completed, the arithmetic processing section 291 having a function as a path calculating section calculates a path line as a segment which passes K-pieces of points including the centroid and the center point of the hypothetical circle, a predetermined position on a distal end surface of the distal end portion 215, and the point Db (step S211 in FIG. 14), and thereafter repeatedly performs a series of processing steps from the step S201 in FIG. 14. Note that the arithmetic processing section 291 calculates, as the path line, a parametric curve calculated by applying Catmull Rom curve equation to each of the points, for example. Specifically, by performing the processing in the step S211 in FIG. 14, the arithmetic processing section 291 calculates, as the path line, a curve Ic passing the points E1, E2, E3 and E4 as the path points, the predetermined position on the distal end surface of the distal end portion 215, and the point Db, as shown in FIG. 17, for example.

Furthermore, the arithmetic processing section 291 performs the processing shown in the flowchart in FIG. 15 in parallel with the processing shown in the flowchart in FIG. 14.

The arithmetic processing section 291 calculates the current position and orientation of the distal end portion 215 based on the three-dimensional coordinate information outputted from the source coil position/orientation detecting section 246 (step S221 in FIG. 15).

After that, the arithmetic processing section 291 determines whether or not the distal end portion 215 has passed through the target position for the distal end portion 215 to be passed, which is set by processing to be described later (step S222 in FIG. 15). When determining that the distal end portion 215 has passed through the target position, the arithmetic processing section 291 calculates a new path line with the predetermined position on the distal end surface of the distal end portion 215 as a starting point by the processing shown in the flowchart in FIG. 14 (step S223 in FIG. 15). When determining that the distal end portion 215 has not passed through the target position, the arithmetic processing section 291 subsequently performs the processing in step S224 in FIG. 15 while retaining the target position and the path line related to the target position.

That is, the arithmetic processing section 291 having the function as the path calculating section performs the processing for calculating a new path line with the predetermined position on the distal end surface of the distal end portion 215 as a starting point, every time the distal end portion 215 passes through the target position set by the processing to be described later.

Based on the three-dimensional coordinate information outputted from the source coil position/orientation detecting section 246, the arithmetic processing section 291 calculates a moving velocity of the source coil $C_1$ per unit time, for example, thereby calculating the moving distance r1 of the distal end portion 215 after Δt seconds (step S224 in FIG. 15).

The arithmetic processing section 291 calculates the target position for the distal end portion 215 to be passed, based on the path line Ic and the moving distance r1 (step S225 in FIG. 15).

In the processing in the step S225 in FIG. 15, the arithmetic processing section 291 sets a hypothetical globe Br1 with the predetermined position on the distal end surface of the distal end portion 215 as a center point and the moving distance r1 as a radius, as shown in FIG. 18, and thereafter calculates the three-dimensional coordinate position of a point Q where the hypothetical globe Br1 and the curve Ic intersect with each other. Then, the arithmetic processing section 291 calculates the three-dimensional coordinate position of the point Q as the target position for the distal end portion 215 to be passed.

The arithmetic processing section 291 of the present embodiment calculates the three-dimensional coordinate position of the point Q as the target position by the processing in step S225 in FIG. 15, and thereafter may correct the target position by further performing the processing steps described below.

Specifically, the arithmetic processing section 291 calculates the three-dimensional coordinate position of the point Q, and thereafter calculates a plane Ha including the point Q and perpendicular to the vector pointing from the predetermined position on the distal end surface of the distal end portion 215 to the point Db, as shown in FIG. 19, for example.

The arithmetic processing section 291 forms a hypothetical circle Br2 having the radius r2, which includes the point Q as the center point and exists on the plane Ha, and thereafter calculates the three-dimensional coordinate position of a point T which exists on the same plane as the path line Ic, among the points on the circle Br2, as a corrected target position.

That is, the arithmetic processing section 291 having a function as a target position correcting section performs the processing steps described above, thereby capable of calculating the three-dimensional coordinate position of the point T as the corrected target position at which the amount of bending of the bending portion 216 can be reduced compared with the case where the point Q is set as the target position.

Meanwhile, the arithmetic processing section 291 calculates the amount of bending and the bending direction of the bending portion 216 such that the distal end portion 215 moves toward the target position set in the step S225 in FIG. 15 (step S226 in FIG. 15).

Based on the amount of bending and the bending direction of the bending portion 216 calculated by the processing in the step S226 in FIG. 15, the arithmetic processing section 291 performs arithmetic operation of the bending control information which is necessary for actually bending the bending portion 216 (step S227 in FIG. 15), and outputs the arithmetic operation result to the bending control section 205. After that, the arithmetic processing section 291 repeatedly performs a series of processing steps from the step S221 in FIG. 15 again.

Note that, when the bending portion 216 includes a plurality of bending pieces and the like connected to one end side of the wire and is configured to be capable of changing the bending state thereof according to the tension or relaxation of the wire caused by the rotational driving of the motors, for example, the above-described bending control information is assumed to be shown as the information related to the angles of the pulleys connected to the motors and the driving voltages applied to the motors. In addition, when the bending portion 216 has an alternative configuration other than the above-described configuration, for example, the above-described bending control information is assumed to be shown as information corresponding to the alternative configuration.

As described above, the endoscope system 201 of the present embodiment is configured to perform the processing shown in FIG. 14 and FIG. 15 in the automatic bending mode, thereby capable of controlling the bending portion of the endoscope such that the endoscope distal end portion is advanced toward (the lumen on) the rear side of the folds forming a flexed portion in the lumen as shown in FIG. 16, for example, while preventing the endoscope distal end portion from contacting the folds. According to such a configuration, the endoscope system 201 of the present embodiment can improve the insertion performance of the endoscope compared with conventional systems.

Note that the arithmetic processing section 291 of the present embodiment may further perform the processing steps shown in the flowchart in FIG. 20, between the step S223 and the step S224 in FIG. 15.

First, the arithmetic processing section 291 calculates a radius of curvature F of the path line calculated in the step S223 in FIG. 15 (step S231 in FIG. 20).

Next, the arithmetic processing section 291 determines whether or not the radius of curvature F calculated by the processing in step S231 in FIG. 20 is larger than a threshold THF (step S232 in FIG. 20). When determining that the radius of curvature F is larger than the threshold THF, the arithmetic processing section 291 performs the processing in step S233 in FIG. 20 to be described later. Furthermore, when determining that the radius of curvature F is equal to or smaller than the threshold THF, the arithmetic processing section 291 uses the path line calculated in step S211 in FIG. 14 as the processing result, and subsequently performs the processing in step S224 in FIG. 15.

When determining that the radius of curvature F is larger than the threshold THF, the arithmetic processing section 291 calculates a plane Hb including the entire path line calculated in the step S211 in FIG. 14 (step S233 in FIG. 20).

After that, the arithmetic processing section 291 projects the three-dimensional shape data calculated in the step S202 in FIG. 14 and the path line calculated in the step S211 in FIG. 14 on the coordinate system of the plane Hb (step S234 in FIG. 20).

Note that the coordinate system of the plane Hb is defined with the axis with the largest variance of the path line calculated in the step S211 in FIG. 14 as a first principal component axis and the peak direction of the path line as a second principal component axis, as shown in FIG. 21, for example. The three-dimensional shape data and the path line representing the shape of the lumen are respectively projected on the coordinate system of the plane Hb as the states shown in FIG. 21, for example, by the processing in step S234 in FIG. 20.

The arithmetic processing section 291 performs transform processing for reducing nearly generally the second principal component of the path line which is projected on the coordinate system in the plane Hb (step S235 in FIG. 20). According to the processing, the arithmetic processing section 291 acquires the path line as shown in FIG. 21, for example, as the path line subjected to the transform processing.

The arithmetic processing section 291 then acquires a new path line by reversely projecting the path line subjected to the transform processing on the coordinate system of the three-dimensional shape data as the coordinate system set by the processing in step S203 in FIG. 14 (step S236 in FIG. 20), for example, and thereafter subsequently performs the above-described processing in the step S224 in FIG. 15.

By further performing the above-described processing steps between the step S223 and the step S224 in FIG. 15, the arithmetic processing section 291 of the present embodiment can calculate the path line for advancing the distal end portion 215 such that the distal end portion 215 passes through the vicinity of the wall surface on the inner circumferential side of the extremely flexed region in the lumen.

Note that, if the determination condition in the step S232 in FIG. 20 and the content of the transform processing in the step S235 are appropriately changed, the processing shown in the flowchart in FIG. 20 can be also applied to the case where the path line is calculated for advancing the distal end portion 215 along the surface (stomach wall) of the lumen having a large diameter such as a stomach, for example.

That is, in the present embodiment, the arithmetic processing section 291 further performs the processing shown in the flowchart in FIG. 20, which enables detailed observation of the state of the surface of the lumen while preventing the distal end portion 215 from contacting the surface of the lumen.

Note that embodiments and the like configured by partially combining the above-described embodiments and the like also belong to the present invention.

What is claimed is:

1. An endoscope system comprising:
   an endoscope including an insertion portion to be inserted in a subject, a distal end portion which is provided on a distal end side of the insertion portion and which includes an image pickup section for outputting an image pickup signal corresponding to an image of a photographic subject in the subject, and a bending portion which is capable of changing a position and an orientation of the distal end portion with respect to an insertion direction of the insertion portion;
   a position detecting section for acquiring position information including at least information on a position where the distal end portion is located;
   a passing target position setting section for setting a passing target position for the distal end portion based on the image of the photographic subject;
   a path estimating section for estimating a path through which the distal end portion is to be passed based on the position information and the passing target position;
   a bending control target position setting section for properly setting a bending control target position on the path such that the distal end portion reaches the passing target position along the path, based on the passing target position and the path; and
   a bending control information calculating section for calculating bending control information on an amount of bending and a bending direction of the bending portion based on the bending control target position.

2. The endoscope system according to claim 1, wherein the bending control target position setting section calculates a moving distance of the distal end portion per unit time based on the position information, and sets the bending control target position based on the moving distance.

3. The endoscope system according to claim 1, further comprising a dark part region detecting section for detecting a dark part region included in the image, wherein the passing target position setting section sets a gravity center point of the dark part region as the passing target position.

* * * * *